(12) United States Patent
Kim et al.

(10) Patent No.: US 9,677,081 B2
(45) Date of Patent: Jun. 13, 2017

(54) PROMOTERS AND METHODS THEREOF

(71) Applicant: Seoul National University R&DB Foundation, Seoul (KR)

(72) Inventors: Ju-Kon Kim, Gyeonggi-do (KR); Su-Hyun Park, Gyeonggi-do (KR); Yang-Do Choi, Seoul (KR)

(73) Assignee: Seoul National University R&DB Foundation, Seoul (KR)

( * ) Notice: Subject to any disclaimer, the term of this patent is extended or adjusted under 35 U.S.C. 154(b) by 196 days.

(21) Appl. No.: 14/666,251

(22) Filed: Mar. 23, 2015

(65) Prior Publication Data
US 2015/0376632 A1     Dec. 31, 2015

Related U.S. Application Data

(63) Continuation-in-part of application No. 13/494,568, filed on Jun. 12, 2012, now Pat. No. 8,987,557, which is a continuation-in-part of application No. 12/583,623, filed on Aug. 24, 2009, now Pat. No. 8,237,018.

(51) Int. Cl.
*C12N 15/82*     (2006.01)

(52) U.S. Cl.
CPC ................................ *C12N 15/8216* (2013.01)

(58) Field of Classification Search
None
See application file for complete search history.

(56) References Cited

U.S. PATENT DOCUMENTS

| 4,940,838 A | 7/1990 | Schilperoort et al. |
| 6,958,434 B2 | 10/2005 | Kim et al. |
| 7,365,185 B2 | 4/2008 | Boukharov et al. |

FOREIGN PATENT DOCUMENTS

| EP | 0116718 A1 | 8/1984 |
| EP | 0120516 A2 | 10/1984 |
| EP | 0301316 A2 | 2/1989 |

OTHER PUBLICATIONS

Sequence Accession AP003831, Feb. 16, 2008, provided in IDS filed Mar. 23, 2015.*
In-Cheol Jang et al., "Subcellular targeting of green fluorescent protein to plastids in transgenic rice plants provides a high-level expression system", Molecular Breeding, 1999, pp. 453-461, vol. 5, Kluwer Academic Publishers, The Natherlands.
Sequence Accession ACL37128, Kreps et al., Jun. 2, 2005.
Sequence Accession AP003831, Sasaki et al., Feb. 16, 2008.

* cited by examiner

*Primary Examiner* — Elizabeth McElwain
(74) *Attorney, Agent, or Firm* — IP Legal Sercives, LLC

(57) ABSTRACT

A promoter, which may be used to transform a plant and/or express a gene substantially uniformly in substantially all organs and/or tissues of a plant, and which may include a constitutive expression promoter for transforming a monocot plant. A vector including a promoter, which may include a recombinant plant expression vector. A method of producing a target protein using a vector, and a method of producing a transformed cell and/or plant using a vector. A transformed plant, a transformed seed and a transformed cell are included, which may be formed by the method of producing the same using a vector.

3 Claims, 8 Drawing Sheets
(4 of 8 Drawing Sheet(s) Filed in Color)

SEQUENCE LISTING

```
<160> NUMBER OF SEQ ID NOS: 54

<210> SEQ ID NO 1
<211> LENGTH: 1673
<212> TYPE: DNA
<213> ORGANISM: Oryza sativa
<220> FEATURE:
<221> NAME/KEY: promoter
<222> LOCATION: (1)..(1673)
<223> OTHER INFORMATION: APX (ascorbate peroxidase)

<400> SEQUENCE: 1
gtaaggtgac atggcatatc tatgtggtga ttttggtggg accaaggact atatcagccc      60
acatgacaaa tttaaaggac ttgtttggac aatatgaaag attaaggact aaaatgacct     120
aggagcgaaa ctttagggac catattggct attctcsctt tttgacacga atgaaaaatc     180
caatttcata acttgtctgg aaaccgcgag acgaatcttt tgagcctaat taatccgtca     240
ttagcacatg cgaattactg tagcacttat ggttaattat ggactaatta agctcaaaag     300
attcgtcttg cgatttcctt tttaactgtg taattagttt ttcttttact ctatatttaa     360
tgctccatgc atatgtctaa agatttgatt taatgttttt cgaaaaaact tttggaggac     420
taaccgggcc taacgtgact tgaagagctg tgacagcgca aatcgtgaaa cgcggatgga     480
cctagcatta tggtgatgta ggaagtgcct tgctggcagt ggcaggtacc gtgcaagtgt     540
aataccatag atccgttggc ttatctgatt acatgatgat gattactccc tccgtttcac     600
aaatataagt catttttagca tttttcacat ttatattgat gttatgtcta gattcattaa     660
catcaatatg aatgtgggaa atgctagaat gacttacatt gtgaaacgga tcattaacat     720
caatatgaat gtggaaaatg ctagaatgac ttacactgtg aaacggaggg agtatacgat     780
tatgtaatga aaaaggagt acaatactag tcgccgtctc cccgcaaaaa aagtactagt     840
tgtcgtcaag taggggagta ataataataa taataataag ggataatata caggctgtgt     900
ttagatcgtg tgccaaattt ttttaaagta tacgacaaa tatttaaata ttaaacatag     960
actaataaca aaacaaatta cagattccat ctgtaaactg cgagacgaat ctattaaacc    1020
taattaattc gttattagca aatgtttact gtagcaccac attatcaaat catggcgtaa    1080
ttagctcaaa agattcgtct cgcgatttac atgcaaacca tgcaattgat tttttttttca   1140 tctacgttta gttctatgca tgtgtccaaa tattcgatgt gatgaaaaaa ttggtaattc    1200
gaggaaaaaa tttaaatcta aacacggcca cagtataaaa aaaaatagta gcgttgttgt    1260
ttatgaaaga ggatggtaaa gtaagacaag ataacgcaag ggcctaaaaa agtggagacg    1320
aagaagaaga cggaatatat tgcattggaa aagtgagcgc ttggacgaga gaaaaactcg    1380
```

```
gattcaagcg tccatatcag tggacaccac caatgggagg tggccacgtg ggcaggtccc    1440
gggtggaatc tggcgcgttc acacgggagg ttccgaaatt acggcaacgc cactggagtg    1500
cgaggcgcag gatgtgagat ccacggcggg ggctccgcta ctagaaactt cttctggtcg    1560
tgggtggtac gcaccctcgc gcctcgcctt tatattacta gtaagaagat ctcatccctc    1620
cttggtgagg tgaggtgagt tgagttgggg attgattgat tgattcggat tgg           1673

<210> SEQ ID NO 2
<211> LENGTH: 1800
<212> TYPE: DNA
<213> ORGANISM: Oryza sativa
<220> FEATURE:
<221> NAME/KEY: promoter
<222> LOCATION: (1)..(1800)
<223> OTHER INFORMATION: R1G1 (Putative R1G1 domain containing protein)

<400> SEQUENCE: 2
atagctgttg tactgatgtc gtgcctaatg aggaaattgg agtaactgtc taactgattc      60
aacagaggaa attaaatcca ggtgagggat gatcagtgaa tccaaatatt gtactaatga    120
tcatgagtat tttatgtggg cattcttctt gacttgaagt tgtaaccgga cataactgct    180
gctaggaatg tatgacttga agcttttaagc actactacat ctgatgatcc ttacatgttg    240
agcaagaggc tggaagaaaa aaaggatgag agccttttaa cccatgtaac tccaatgctg    300
tctgcaaacc tttcagctgg ttgtgagttg tggctgcaga tctgtggaag ccactgagag    360
agcactaggt aaggtttcta tgttatatct gtaattctgt atatgtttaa tgtgttgtgc    420
tcatttaaaa aaagaactgc atagattcac aaactgcctg gagctttcct cttcactttg    480
ctaatagtat tgaccacgtt ttgggcttgt tgtgtgtttg aaggagtgg gtctataggc     540 cgtcagtgtt taggcctact aattaagcca gttcagttgg gccttggctg cttccatgga    600
ttaattatga gactaatcgc agatactcgt acaccaatgc gagaatttgt caaatcaatt    660
ggatcagtat atatcttgcc tgtatgattc acatccatac gtttctatcg agttggttgg    720
aagatttgtg ccgtcgatga cagtgcagaa gagaagcttc cttgcaacta gtgtcgtggc    780
agaagcagag gtagacacat gaaatcgtgt tctaatccgt cgcagctagc tagcatggca    840
gcgacgtgtt tgacgatgac accaccttgc atatccagat gcctctgttt gacctggatg    900
gaacaaacaa taacgtacgt ttttcgagca tctaaatggt ataaattttt agagaaattt    960
ttatgtgtaa tttctttctt ataatatagt tttaaaatct gtttcacaac taatcaattc    1020
agtcgtttgt atcctcgaat catttcatg ttcaacattc catccattta ggcatttatg    1080
cacagaacag tagaatacat agtttgtcca tgctttaaac gaaaagtaaa aagaaagag    1140 aaagacacat attcctctta aaacaatatt cgtttgagat ggtggaggga acaaaggcca    1200
ttgatttgct gcagggtccc tccctaacaa gctgtgatga ttctgtatac gacgatcgtg    1260
caattaagct agtgctttga agagacaga cagacagaca acttttttcc tcctaatacg    1320
atcggaagaa aactgtcgag cttttatgta gcgtataaac cttgactgtt gcgaggaaaa    1380
aaaagctgta ggaaacaaag aaatcgagga aatgaatttg tcctggtttc gtatatatgt    1440
acatgtacta tatgccaaaa acgcccgtgc ttaacagcta agaaatcggc caaaattcag    1500
gcaaacaaga gacaaagtta gcaggcaacg cgtcactacc gcgtgatcat ttcgacgcga    1560
aggcaatttg gccggtgatc cagcgcgtct cgtgcagtga atgaagtagc ttaatttgct    1620
agtccccaca agtacgtggc actctgccat gtcttctctt agtataaata tatggaagcc    1680
aaagccaaag ccagtcagtt catcagttgc agttcagagt tgcccactgc tactttactt    1740
```

```
tgcagctatt ttgcttctgc ttcttcttgt tcttgttgct gttggtaata ctgcgagaga    1800
```

<210> SEQ ID NO 3
<211> LENGTH: 1813
<212> TYPE: DNA
<213> ORGANISM: Oryza sativa
<220> FEATURE:
<221> NAME/KEY: promoter
<222> LOCATION: (1)..(1813)
<223> OTHER INFORMATION: PF1 (60S acidic ribosomal protein P1)

<400> SEQUENCE: 3

```
ctcggtgaag atagagaagg tttagaaaat acatggttga acccaacaat tgtaccaagt      60
tcctccaccc attcaacgaa ttggccttca tcttttggct actaaaatca gcccatgacc     120
cccccccccc ccgcctcgat gaatattttt ttgccacttg ccttctctta tttgatgact     180
ctactgcgga caagattctt ctaacatatt attgcccctg atatgatcac taatatgtgg     240
aggtcatcgt caatcgtcca catgactctt taagtaaatt aagtaaaagg atctcaatct     300
ctcaggtgtt gtctcttccc tttgattgct tgagtacctt ggtggctatt tgtgtctttt     360
gacttgaaga atgggtgcgt tcgtctcgtt tgccgtgagt ctacaaaact atgagcttcc     420
tctaattcaa acccgcgtgt ttctaatcct cttcgtctca tagcctacaa cgcaagagtc     480
ttgatggttt atttctttta ccacatcatg tgacgcttac gatgttagtt tattatagat     540
ataatgcaca atttgttact ctattagtta acatgcaaag ttttgtagca gtagcctcct     600
atcatatctt gaaagttttt ttttacattc atttattttg cacgagaaat cctaccgtat     660
ccttatgttt ttggtacact cttgtgtttc caaggagcgt tgactattcg gcttgaataa     720
aggtgtgttt ggttgggtgg atggagcatg gataggagat ggccacccga gttttttgtgg    780
tgtttggttg gagggcaagg tggatggggc agcctagaat agggaatatt ccctcaatat     840
gctggatgag tgcatccggc cgatttggct ggatgaatcc atccagtttt ggactgggtg     900
atatgtccta ttccgattgg ctgtggttgg tttgatttcc tgttaagcaa gctccaaatg     960
atttttttct cctaaactgt ttgtctaatt tatgatttga ttacaccatt atattcgtta    1020
taattaaatc tttaaaacaa gatttcggat gattatattt tgataaaaaa aatatatatg    1080
ataaatgagt cccactaact tttggctttt cgtatctatg ctatatccct ccaaccaaac    1140
aagaaattgg atcgccatat ccatacaaac caaacagaaa attggatcgc cgtatccaat    1200
aaaatatgga tgaccatatc ctatccatgc atgaccgtga atcaaacaca ttataatagg    1260
cctccactca cgaatctgat catgggcttg tgcctgccag cctatgcatc attacttaat    1320
gggcctggac ccttaaattg tccaagttca tcacgcaaac aagatgtggc ccgtatcgga    1380
gattccctca acgaaaaggg cccatctccc ccgggctgct cggacgatgg cccacatact    1440
cacggcccac cgtatcctat cgtgccctat ccaaacacgc gcaaacaccg cacgtgcctg    1500
acccaaactc cgcaaacggg ccggatccga accagacgag gccacgatc cggcccaaga     1560
ggagaaaccc tagcgaggaa gggagtgcct cctacccgct ataaattccc agccacgccg    1620
cctcctccca aaccctagaa gccccctgc ctcctgcgcc tccgccgccg ccgccttctt     1680
cgtctgctgg tacgccgccc ttcgccgccg ccgcctccgc atccaatctg cgttgttctt    1740
ccgccgattt cgattgcctc acccttcgtt ttgtttcttg attgatctcg cagagttcgt    1800
agatcagctc gag                                                       1813
```

<210> SEQ ID NO 4

<211> LENGTH: 1774
<212> TYPE: DNA
<213> ORGANISM: Oryza sativa
<220> FEATURE:
<221> NAME/KEY: promoter
<222> LOCATION: (1)..(1774)
<223> OTHER INFORMATION: PF4 (40S ribosomal protein S8)

<400> SEQUENCE: 4

```
tctggcatcg atatgctcct tccattcatc ctgagagtga gacatgtttt tttctatgtt      60
atgtgcgtgg ttttattggg taaacattgt agaaagacag tcgggcgaca tcggcttata     120
ctaaggggag aatatatgct gggaagagaa cttgaagggg actaattctg attatttatt     180
gctaaattcc aaagactagc taaatacccct atatatagag ccgacacctg caactcaatc     240
taatctaatc ctacttttaa gcaacagagt atatgtaaca cgcgctgcat tggaggcatg     300
gaggcattat atctaacacc caccttgttt ccctgcatgg aggcattccc tagtttacta     360
gcttgctcag tccgtttttgc tcctttcaat ctcaaaatta tatagatcct tatgtttgat     420
gttatttttg tcattaccgg tctcttcacg ttattccatt atgttaggtg ccaagaagag     480
tatgttggac cattagagtg gacatgatta gggatgcaag tggatagttc ctctactcgc     540
aaaaaaccc gtttgctagt tcatttctta catgatagta taaaatttag aagaaaaaat     600
gaagtagaag tgagattagc gggctaaaga aacccgcttg catccctaga catgatccat     660
ccaccttctt attattaggt tgtaggctgc cattttctta ccagccattt acaagattgc     720
caaccagatt cgctctgctc tcgtagccac tttacaccac tacgcagaac tacaaatcta     780
caggatggat ttgcattgcg agcatgatgt ccccaacttt aatacaaaac tgccaatata     840
taatgagttc agcaacgtgt tagggtaaag tttttttttt tttttgcgc agaggcagtt     900
ggaaaaaaaa acctaagacc cctatcccat ataaaaaaaa ccaacttgta gcttacaaac     960
ctagataata agctagaagt ttattttta tgagtaaaac aggtggcttg acagtaattc    1020
tgatggcagt gttcttttga agggattgga gcatatccca ctcgcacgca acaaagtga    1080
caaattaatg cacgattaat taagtattag cttaaaaagt ttgaaaaatg aattaatttg    1140
attttacag taacttttgt gtaatttttt ttaaaaaaag tgcaccattt aaccgtttgg    1200
gatatgtgca tgtggaaaac aagaaatatg tggttgaaac cttgagggag aacacagcca    1260
aaacaaaaaa aaatctgatg gaatcaagaa ggccaacgtt ggtgtgggcc gggcccaatg    1320
catcatttcc ttcgtacgtt gcaatctagg cccaacggac tgcccaccac ccccctcgcc    1380
tgaagaatgg ggtggatcag atggcaggct cattcccagc cgtcggatcg acccgatcac    1440
cgcctgcgaa gtaaacccta agccacggcc gcctccctat ataagcccac ccactagggt    1500
ttcgcccgcc tctcctcccc ccgctagtt cccaaccagc agctgcggcg gcgcgagcac    1560
acgaagagga ggcggagcag ccggagccac ctccgccgcc gccgccacca tgggtaaggc    1620
acgcccgcaa cccgggtgct caaccttcct cctccgctta cccccatccg cgtgggggt    1680
tgtggagttc gttgtttggg ttttttgcgt gtgtgtgtgc tgatggattg atgggggtgc    1740
ggtgatggct gtgcaggtat ctcgcgtgac tcca                                1774
```

<210> SEQ ID NO 5
<211> LENGTH: 1753
<212> TYPE: DNA
<213> ORGANISM: Oryza sativa
<220> FEATURE:
<221> NAME/KEY: promoter
<222> LOCATION: (1)..(1753)
<223> OTHER INFORMATION: PF6 (Ribosomal protein S26E family protein)

<400> SEQUENCE: 5

```
ggaccaaccg aagtccttcc ggaggaaaga ggggaaaaat ccgagcaagc gagcaagctc    60
aggttgccac cggtgacact tcacctgagc aagctcgctc ggtctctaca ggttgcttta   120
tctgaacgca aaagcgatat tccatggaaa agctctcagg cccacggcct cattagacaa   180
ggcccaacgc tcaagtttct ttgaggcggc acatttagat aaggaaatgt ctgagggaat   240
aagatcacgg aggtccctca acctaacagc gagatgagat ttttgagatc ccttacccct   300
aaactcacat aaaccatgca atcaaagtcc tatgatagta tatatgagcg gttttgctga   360
cgtggcatcc tagtcagtca aataaaaaac aaaaaagtta tggggcctaa aagtaagtga   420
gaaggaaaaa atatgagacc cacatatctt cctttctct ttcttctcct ctcttctctt    480
tgccactgag ggggagcggc agcaggcgga gacaaggaac cggagcaggc aggcgagtgc   540
tcggcggctg acggagtgga gcggggtggt ggcagcaggc gagcgcacgt ctggagcagc   600
gtggctgtga gcgcgcgacc gacacagtgg agcggcggtg gcaagcaagt gatgttgcga   660
gtgcgactag tggagcggag cgggcagtgg tggcgcgggt gctcggcgac gccgacgccg   720
tcgcgcttgg ccacggccac gccaccaacc acctccccct catctcctcc tcctcttctt   780
cctcttcccc aaactgcgac atctgccagg agacccacgc ctacttcttt tgcgtcgcgg   840
atcacgccct gctctgtcgg acctgcgaca gcgtcgtcca catcgccaat gccttcatct   900
ccgcccattg caggttcctt ctcaccggcg tccacgtcgc cccttgacac cacccctctg   960
ctccttcgca cctggagcca ctgttcgctc gccgcgtccc aagcccctct gcacctcctg  1020
agcccggagc cgccgctcgc ccgccgacgt cgccgctccg cctgcctccg gccgcacgcc  1080
gccgctgctc cccttctacg gcaaatataa aaatgaagag aagaagagaa aaagtaaaag  1140
agcggcaaag ataaaaatga agagaagaag agaaaaagga aaagagaagg agattggtga  1200
ctagatcgtt gaccacatat ttttttttctc acttacatgt ggatcccaca ttttttattta  1260
ttttattta tgctgattag gatgtcatgt cagcaaaatc gggcaaaaat tgagtcgata   1320
ctgccatggg acctcctttg aacggtttga gtgagtttag gggtacaaat ttctggttct   1380
gtggttaagg gacctaaaaa attctcgctg ttaagttgag ggatctccgg tgaacttatt   1440
gcaatgtctg agagacaacg aagtgataga ttgggcctcc agcccacgag agtagaagtc   1500
ccagtcgcac gtttcgtcgc ctataaatac tctcccccctt gggcagccac aaaccctagt  1560
cgaggagagc acccaacccc tgcgccgcca cctccgatcg tcagccatgg taaggagctc   1620
gccgcttccg gatccaccct agccgccgcg gcggcggcgg ccgcttcggc gtcttcttct   1680
tctccgctca atctcccggt tagtcccttc tgattggttt cctcctttcc ctcgcagacc   1740
ttcaagcgca gga                                                     1753
```

<210> SEQ ID NO 6
<211> LENGTH: 1978
<212> TYPE: DNA
<213> ORGANISM: Oryza sativa
<220> FEATURE:
<221> NAME/KEY: promoter
<222> LOCATION: (1)..(1978)
<223> OTHER INFORMATION: SC2 (Histone H3.3)

<400> SEQUENCE: 6

```
ttacgtatag ccttttcctt cggttttccc tggctgacga gtgacaaaac tgcagttgag    60
cacatgcggc aaaagaacac ccccagcgtc atcgtgccac gtggatggcc cccgcaccaa   120
```

```
atcaaacggc ccccgcgaga ggaacgccac aaccaacctc tccccctcct ctccgcagcc        180
gcacactccc gtcacgttgc ggtacggaca cccacacaca cagagacacg ctccgcctct        240
cactgatccg tgggaccacc gatccgcggc acgccagttc gggccaatca gagcccaggg        300
atccacgctg gcgatccgcg ggcagtcact cacccccgg ctcccacccc caccgccgtc         360
cgatcgtggc ggaggaaaca cacccgcgga cgatctcggc cgtccgacca cgcgggcgga        420
tataccaacc gggcgggggg tgggggattc ctcgctataa ataggaggcc gccgcttggc        480
tgagcaattt ttctgcggtt tcttcttctt cttcctcctc ctcgcgctcc cccgattcga        540
agcgtgaaga gaggaacggc gcttgcgaga ggagagaggt aagcatcacg gcgaagtttc        600 ccctctctc tttcttttcg tctcgtttgc tgcgaccccg gcggggtatt gagattctcc         660
gttgaggtcg gttggttggg ggcttggggg attgggtggg ttagggcttg ggggtggggg        720
gaatttggcg atttgggggg ttttctcggg tgatctgctt gttttttgcgc cgtttcgccc      780 ggtgaatgcc agccccgtgt gatttgctgg tttggttgtg gtctaatcgt ctgatattcc        840
agggctgtgt agtcctgtag tttttgacta ggtaattgga gtgctgatgg gatttgccgt        900
tgaattttag gttgtttagc tctaatttac ctgcaacgtt ttgggaatta gggtttcttg        960 gtgaattta ggttgtttag ctttaattta cctgcaacgt tttgggaatt agggtttatt       1020
ggtgatatag tggatacgca tcgtaaactt gtatttagga ttccccttgg gattttgtag       1080
gcgagtggcg gctgtatgtg attggcacga attatttact cgggtgaatt tagactagct       1140
attttattgt tgccgtgccc tttctggata tgaacggatg aatatggcgt cactgctcga       1200
tgatatcgca atgttatgat tgaaaaagca tagtagttat actgatgcca ttgtgtagta       1260 gttagttttgt acctcccctg ggttgcattg caacttgcgt taatatggat actccgtaca      1320
attgtttatt gtttacttgg tatagctatg ctgcattttc tatatttgtt gggttataag       1380
tttttgtcca atatttttaa tgacttgtgc cagaggctct caatcctctg ttattagacc       1440
tgtaattgta aggtctattt ctccttcatt ctgtttcaat gttagtttgt ggatgtacag       1500
aaatcaagct atgattgata taatacattg ctttggcata atggcactct tattttttgtt      1560 ttatttagga gagtgctgtg tattagtttg ttcagttaat tcaatgttgt atgttttact       1620
gtgtcgggaa cttacagatg ttctctttag gtttctatcc attagtaagt agagttgttg       1680
ctttgcttga aaccatcaat ttgaatctgt ttatagagat aggctgttat tcctgcttac       1740 tatttttttat atagttactt tgccatccgt taatcaggtt aagaacaata aattgtgtcc      1800
ataatcaatg ttttcaatgg aactcacaaa attttgacag aaacatgttg ctttcttagg       1860
tcaatctcta gcatattgtt ttttttttga attgttactt gtttctgtgg tgttattaca       1920
gaaagtgctt acttccactc tagaatttta ttacattttt gtcacagcat attctgtc         1978
```

<210> SEQ ID NO 7
<211> LENGTH: 1906
<212> TYPE: DNA
<213> ORGANISM: Oryza sativa
<220> FEATURE:
<221> NAME/KEY: promoter
<222> LOCATION: (1)..(1906)
<223> OTHER INFORMATION: SC5 (60S ribosomal protein L9)

<400> SEQUENCE: 7

```
tgtgacgtgg cagtctgaca cgtggggtac atgctgactc agctgccacg taggataaaa         60
acgggctcaa aaccaccgaa tgagttattg taaccggttt tggtaagtta aggaaccttg        120
atatctggtt ttgcggttcg aggacgtttt ttatctcggt agcaagttga gggaccttcg        180
```

```
gtgtactttt ccgaacgtga aatgggtggt atcatgatgg gctgttcaat ctgtcgatat    240
ttatgggctg aattaggctt acaggcttag ggcaagccga atttcgtggg ctattatggc    300
agcttttctc gtgcacaaat atggatcttt atttggccca ccgcgacccc acggcataac    360
gaaacaggca gagcccctgg aaagatttca gcaatacctg ttcagacgac gacgtctgct    420
ctgttgttcg atttccgtcc gcatattcgt cgtgtgatcg tgtccacgcc tggagttttc    480
tggcacaggc cgcgctcttc tcacctcagc ctcaggactc aggtgatcgt gtcaacgtcc    540
ggagctctca ggcgatcgtg tctcacttca caggttgaca ggtcggcgca ttcgatgccg    600
ttccaaacgc agaaaattta gagaaacatc tcgggacaga gcggcgctcc cacgcgtgga    660
atcccgcaga tgtaaaactt cgttacaatt tacagtgttc gcaacatcaa gaaacgacat    720 ttttttcattc gaaaatgctg caaatctgca actggcaatc tctagacaaa tccttttccct   780 ttcgatgccg aagcagaatt gaagtttgag aatgttcttc gtctagaccg agcagtcagt    840
gatctgcaag cgcgaggcgt tcacagatcg tctcgacgac ctccctcccc tgggacgcgt    900
tctgcctgaa cctctccgcg caccgccgct ccaccatctc ggccgcccag ccgccacgg    960 cagcgagcgg cgcgcaccga atgctcgtct cctgccggaa cagcgtccac tcgtcgggcc   1020
gctccgggtg cgggcggtag ctgcaggtct cctcgacgtg caccagcgcc cggaggttgg   1080
cgttgcggga gatcacccgc atgggcgtg cgggcccgtc cacggtggtg tgctcgacgc   1140
agagcaccac gtcggcggcg gcgacgaggc cgcggaggag gagcgggagc ggcggcgccc   1200
gccccgcgat ggcgcgcacg gcgtcgatgc gccccgatcc agcgtcgacg cggcgggaca   1260
gcgtgtgcac ctcgaggatg tgcgacagcg gcgccgcccg cgcgtccgcg tccgtgaact   1320
tgcgccacgc cgccgcggtc acccggtgcc acgggtggcg gtacacgtgc tcctgcgtgt   1380
acgagaccac catgccggcc ggccggccgc cgcttgcctg tgcgcgcgcg cgtcgcgtcg   1440
cgccgagatc gagcgaggct agcgagagcg atttcgacag caactgcagc gaaataatgg   1500
gaatatgagt gtgtgtggac tccggactcc ggaggaagag aggaatattc gagttccacg   1560
gggaattaaa cccattattt tgggctcaat ttgcttggac tgcaaagcta ccagacctgc   1620
agcccagcgc atctacagat gggccaaatt ttgacatact tcttagtggg cctaagaatt   1680
catgaattgg ggccggccta aggccagcag cccagtgagt catcacctcg cgacctaatg   1740
tctcgatcca acgcgaagaa tcaaaaccct aacctgcgcc atcgtcgact atattaaaag   1800
cccactcctc cccgcgccgc cgcccttctc tcgagcaagc acccaaaccc tcccctctac   1860
cccgccgccg ccgccgagga aggggcaaga ggaagccggc gaagat              1906
```

<210> SEQ ID NO 8
<211> LENGTH: 1876
<212> TYPE: DNA
<213> ORGANISM: Oryza sativa
<220> FEATURE:
<221> NAME/KEY: promoter
<222> LOCATION: (1)..(1876)
<223> OTHER INFORMATION: SC7 (Histone H2B.1)

<400> SEQUENCE: 8

```
gtcgaactca ccgtgcacta tatcaaccgc cgaagaaata aattcttcgt caccatccga     60
tgaaaactca tccaatagca tttggaggag ggtgcttcga cgactcatct cctctttttg    120
tttgccacgg tgttggagcg tttaccacag ggatgaagtg caatggaggg aactgatggc    180
aggaatagaa caataatcaa tctgcaaaat taattatcag atcaaactta atatttttcca    240
```

| | |
|---|---|
| acaatatata tccacatcaa atactgaca tagagattga ctacggcaca agagattaat | 300 |
| gggatttgct aaggattacc tccttgatga cacgaattgc tacgacatct ccttggtgtt | 360 |
| ccgttttta acaaatcgca gcagtcagga cactggttgg ctggctggtg atgatggcgc | 420 |
| taggtcacgg cggcgcaagt gtggggagga agaagtcgat cggcgctggt gcggagggaa | 480 |
| gaagacgtgc gcaagtaccg aactgggccc caccttgctt atgtggcaaa ctaacaaatg | 540 |
| atagggaatt gatttttggg cttctcttgg aggaggggt cattgttggg cccaattttt | 600 |
| attttggtat tcctaattca gattttttgg gaatcaaata ttgggtgatt gttgggcatg | 660 |
| ctctaagtga tttgtttggt tgggagacat ggaaaattta gtgggatagg gatggtgaat | 720 |
| tgaggaagga actccctcct tttcaatacc tgggtagggg caggtaattg ggagggaatt | 780 |
| cctcctttac tttttctaag caaatctgag ccatctgttt ttattaatga cttaatctcc | 840 |
| aactaaactc cctatcaatt tccattacct ctaccaaaca agatattgag attaaaaatc | 900 |
| aaattcccat cttaatctca ttatcaattc cctcgtgtaa actcccaatc tccttccctc | 960 |
| gagttaccaa acaagccgtt agatcactaa gaatacgtat ataaaagttt tattcacaaa | 1020 |
| ttttttccat ttacaaatat gccgatgggt cctggtgatt tacttaacaa atgtttgatt | 1080 |
| agatcttcag ttttatatac aaattcgttt tgtctaaaca gataaaattg acttattaat | 1140 |
| cttgggaagg ccgttactca ctctagactt tactcctcct tatcttttt tttcttgaac | 1200 |
| gaacatttca tttcttatat ttttgcatag tttttttaag gtagttatag acaaaagtga | 1260 |
| taatgattgg gcttctaaat aatgggtaag acttgtctcc aacaagtgac ccataagggc | 1320 |
| acctaaatct aaaatgggtt tccgatagta ttatttcagc ctccaacaga gtacctatac | 1380 |
| agaagaccta ttttacgtgc tataagaggc ataacctaaa tctgagtatc ctctctcctg | 1440 |
| aagacctatt tgcagtaagg gttctctttt aggccttatt gttggagaag accaaaaata | 1500 |
| ggtattgaac tcttttactg tagcgctatg caaacgtgaa atgagtcttg tatttgggt | 1560 |
| ttcattgttg gagatagcct aaccaccacg cgccggaagc caaacccagt tctccccgtt | 1620 |
| cccgcctaca ttttcgccac gtcagcgatc cgcaccgaaa tgcatcgcag ccgtttacgg | 1680 |
| aaacagcatc gaacgtcaca cgttcgtcca cgttatcgat ccgtggggaa accactccac | 1740 |
| caatcagcgc ccacctcaag ttcgctataa agtcgtcgcc ccgtcccca ttctcttccc | 1800 |
| cacatcgcag tcttgcaaac acacgcagca aaatccacac cgcttcccct ccccgagaag | 1860 |
| aagagagcag catcca | 1876 |

<210> SEQ ID NO 9
<211> LENGTH: 20
<212> TYPE: DNA
<213> ORGANISM: Artificial Sequence
<220> FEATURE:
<223> OTHER INFORMATION: APX forward primer

<400> SEQUENCE: 9
gacctctaga ccgccgtatt                                                  20

<210> SEQ ID NO 10
<211> LENGTH: 20
<212> TYPE: DNA
<213> ORGANISM: Artificial Sequence
<220> FEATURE:
<223> OTHER INFORMATION: APX reverse primer

<400> SEQUENCE: 10
gccaaccact cgcaatccaa                                                  20

<210> SEQ ID NO 11
<211> LENGTH: 20
<212> TYPE: DNA
<213> ORGANISM: Artificial Sequence
<220> FEATURE:
<223> OTHER INFORMATION: R1G1 forward primer

<400> SEQUENCE: 11
cttctcgatt gccgtgtgct        20

<210> SEQ ID NO 12
<211> LENGTH: 20
<212> TYPE: DNA
<213> ORGANISM: Artificial Sequence
<220> FEATURE:
<223> OTHER INFORMATION: R1G1 reverse primer

<400> SEQUENCE: 12
gcaagtctca agctctcaat        20

<210> SEQ ID NO 13
<211> LENGTH: 20
<212> TYPE: DNA
<213> ORGANISM: Artificial Sequence
<220> FEATURE:
<223> OTHER INFORMATION: PF1 forward primer

<400> SEQUENCE: 13
ggtctcttcg ccaagctcct        20

<210> SEQ ID NO 14
<211> LENGTH: 20
<212> TYPE: DNA
<213> ORGANISM: Artificial Sequence
<220> FEATURE:
<223> OTHER INFORMATION: PF1 reverse primer

<400> SEQUENCE: 14
cgcctcctcc ttcttctcct        20

<210> SEQ ID NO 15
<211> LENGTH: 20
<212> TYPE: DNA
<213> ORGANISM: Artificial Sequence
<220> FEATURE:
<223> OTHER INFORMATION: PF4 forward primer

<400> SEQUENCE: 15
caatgtggca gagctgatgg        20

<210> SEQ ID NO 16
<211> LENGTH: 20
<212> TYPE: DNA
<213> ORGANISM: Artificial Sequence
<220> FEATURE:
<223> OTHER INFORMATION: PF4 reverse primer

<400> SEQUENCE: 16
ggtctgtagg cacgacatag        20

<210> SEQ ID NO 17
<211> LENGTH: 18
<212> TYPE: DNA
<213> ORGANISM: Artificial Sequence
<220> FEATURE:

<223> OTHER INFORMATION: PF6 forward primer

<400> SEQUENCE: 17
gaagctgtac gccaaggt                                          18

<210> SEQ ID NO 18
<211> LENGTH: 20
<212> TYPE: DNA
<213> ORGANISM: Artificial Sequence
<220> FEATURE:
<223> OTHER INFORMATION: PF6 reverse primer

<400> SEQUENCE: 18
taggtgcgag caacattagg                                        20

<210> SEQ ID NO 19
<211> LENGTH: 20
<212> TYPE: DNA
<213> ORGANISM: Artificial Sequence
<220> FEATURE:
<223> OTHER INFORMATION: SC2 forward primer

<400> SEQUENCE: 19
ctgcggaggc ataccttgtt                                        20

<210> SEQ ID NO 20
<211> LENGTH: 20
<212> TYPE: DNA
<213> ORGANISM: Artificial Sequence
<220> FEATURE:
<223> OTHER INFORMATION: SC2 reverse primer

<400> SEQUENCE: 20
acactacgac gcatgcttca                                        20

<210> SEQ ID NO 21
<211> LENGTH: 18
<212> TYPE: DNA
<213> ORGANISM: Artificial Sequence
<220> FEATURE:
<223> OTHER INFORMATION: SC5 forward primer

<400> SEQUENCE: 21
catcttgcgg tcggagaa                                          18

<210> SEQ ID NO 22
<211> LENGTH: 20
<212> TYPE: DNA
<213> ORGANISM: Artificial Sequence
<220> FEATURE:
<223> OTHER INFORMATION: SC5 reverse primer

<400> SEQUENCE: 22
tacgcatcct ctgtgatggt                                        20

<210> SEQ ID NO 23
<211> LENGTH: 18
<212> TYPE: DNA
<213> ORGANISM: Artificial Sequence
<220> FEATURE:
<223> OTHER INFORMATION: SC7 forward primer

<400> SEQUENCE: 23
cgtcaccaag ttcacttc                                          18

```
<210> SEQ ID NO 24
<211> LENGTH: 22
<212> TYPE: DNA
<213> ORGANISM: Artificial Sequence
<220> FEATURE:
<223> OTHER INFORMATION: SC7 reverse primer

<400> SEQUENCE: 24
ccacctaatt cttcttacag tc                                              22

<210> SEQ ID NO 25
<211> LENGTH: 20
<212> TYPE: DNA
<213> ORGANISM: Artificial Sequence
<220> FEATURE:
<223> OTHER INFORMATION: PGD1 forward primer

<400> SEQUENCE: 25
ccgtgagcta gcgaggatct                                                 20

<210> SEQ ID NO 26
<211> LENGTH: 20
<212> TYPE: DNA
<213> ORGANISM: Artificial Sequence
<220> FEATURE:
<223> OTHER INFORMATION: PGD1 reverse primer

<400> SEQUENCE: 26
ccggtaggag tcgaagtacg                                                 20

<210> SEQ ID NO 27
<211> LENGTH: 20
<212> TYPE: DNA
<213> ORGANISM: Artificial Sequence
<220> FEATURE:
<223> OTHER INFORMATION: OsCc1 forward primer

<400> SEQUENCE: 27
actctacggc caacaagaac                                                 20

<210> SEQ ID NO 28
<211> LENGTH: 20
<212> TYPE: DNA
<213> ORGANISM: Artificial Sequence
<220> FEATURE:
<223> OTHER INFORMATION: OsCc1 reverse primer

<400> SEQUENCE: 28
ctcctgtggc ttcttcaacc                                                 20

<210> SEQ ID NO 29
<211> LENGTH: 20
<212> TYPE: DNA
<213> ORGANISM: Artificial Sequence
<220> FEATURE:
<223> OTHER INFORMATION: Act1 forward primer

<400> SEQUENCE: 29
atggtgtcag ccacactgtc                                                 20

<210> SEQ ID NO 30
<211> LENGTH: 20
<212> TYPE: DNA
<213> ORGANISM: Artificial Sequence
<220> FEATURE:
<223> OTHER INFORMATION: Act1 reverse primer
```

```
<400> SEQUENCE: 30
taaccacgct ccgtcaggat                                              20

<210> SEQ ID NO 31
<211> LENGTH: 20
<212> TYPE: DNA
<213> ORGANISM: Artificial Sequence
<220> FEATURE:
<223> OTHER INFORMATION: OsUbi forward primer

<400> SEQUENCE: 31
atggagctgc tgctgttcta                                              20

<210> SEQ ID NO 32
<211> LENGTH: 20
<212> TYPE: DNA
<213> ORGANISM: Artificial Sequence
<220> FEATURE:
<223> OTHER INFORMATION: OsUbi reverse primer

<400> SEQUENCE: 32
ttcttccatg ctgctctacc                                              20

<210> SEQ ID NO 33
<211> LENGTH: 32
<212> TYPE: DNA
<213> ORGANISM: Artificial Sequence
<220> FEATURE:
<223> OTHER INFORMATION: APX promoter forward primer

<400> SEQUENCE: 33
aaaaagcagg ctgtaaggtg acatggcata tc                                32

<210> SEQ ID NO 34
<211> LENGTH: 32
<212> TYPE: DNA
<213> ORGANISM: Artificial Sequence
<220> FEATURE:
<223> OTHER INFORMATION: APX promoter reverse primer

<400> SEQUENCE: 34
agaaagctgg gtccaatccg aatcaatcaa tc                                32

<210> SEQ ID NO 35
<211> LENGTH: 32
<212> TYPE: DNA
<213> ORGANISM: Artificial Sequence
<220> FEATURE:
<223> OTHER INFORMATION: R1G1 promoter forward primer

<400> SEQUENCE: 35
aaaaagcagg ctatagctgt tgtactgatg tc                                32

<210> SEQ ID NO 36
<211> LENGTH: 32
<212> TYPE: DNA
<213> ORGANISM: Artificial Sequence
<220> FEATURE:
<223> OTHER INFORMATION: R1G1 promoter reverse primer

<400> SEQUENCE: 36
agaaagctgg gttctctcgc agtattacca ac                                32

<210> SEQ ID NO 37
<211> LENGTH: 32
```

<212> TYPE: DNA
<213> ORGANISM: Artificial Sequence
<220> FEATURE:
<223> OTHER INFORMATION: PF1 promoter forward primer

<400> SEQUENCE: 37
aaaaagcagg ctctcggtga agatagagaa gg                              32

<210> SEQ ID NO 38
<211> LENGTH: 32
<212> TYPE: DNA
<213> ORGANISM: Artificial Sequence
<220> FEATURE:
<223> OTHER INFORMATION: PF1 promoter reverse primer

<400> SEQUENCE: 38
agaaagctgg gtctcgagct gatctacgaa ct                              32

<210> SEQ ID NO 39
<211> LENGTH: 32
<212> TYPE: DNA
<213> ORGANISM: Artificial Sequence
<220> FEATURE:
<223> OTHER INFORMATION: PF4 promoter forward primer

<400> SEQUENCE: 39
aaaaagcagg cttctggcat cgatatgctc ct                              32

<210> SEQ ID NO 40
<211> LENGTH: 32
<212> TYPE: DNA
<213> ORGANISM: Artificial Sequence
<220> FEATURE:
<223> OTHER INFORMATION: PF4 promoter reverse primer

<400> SEQUENCE: 40
agaaagctgg gttggagtca cgcgagatac ct                              32

<210> SEQ ID NO 41
<211> LENGTH: 32
<212> TYPE: DNA
<213> ORGANISM: Artificial Sequence
<220> FEATURE:
<223> OTHER INFORMATION: PF6 promoter forward primer

<400> SEQUENCE: 41
aaaaagcagg ctggaccaac cgaagtcctt cc                              32

<210> SEQ ID NO 42
<211> LENGTH: 30
<212> TYPE: DNA
<213> ORGANISM: Artificial Sequence
<220> FEATURE:
<223> OTHER INFORMATION: PF6 promoter reverse primer

<400> SEQUENCE: 42
agaaagctgg gttcctgcgc ttgaaggtct                                 30

<210> SEQ ID NO 43
<211> LENGTH: 32
<212> TYPE: DNA
<213> ORGANISM: Artificial Sequence
<220> FEATURE:
<223> OTHER INFORMATION: SC2 promoter forward primer

<400> SEQUENCE: 43

```
aaaaagcagg ctttacgtat agccttttcc tt                                     32

<210> SEQ ID NO 44
<211> LENGTH: 32
<212> TYPE: DNA
<213> ORGANISM: Artificial Sequence
<220> FEATURE:
<223> OTHER INFORMATION: SC2 promoter reverse primer

<400> SEQUENCE: 44
agaaagctgg gtgacagaat atgctgtgac aa                                     32

<210> SEQ ID NO 45
<211> LENGTH: 32
<212> TYPE: DNA
<213> ORGANISM: Artificial Sequence
<220> FEATURE:
<223> OTHER INFORMATION: SC5 promoter forward primer

<400> SEQUENCE: 45
aaaaagcagg cttcctcttg ccccttcctc gg                                     32

<210> SEQ ID NO 46
<211> LENGTH: 32
<212> TYPE: DNA
<213> ORGANISM: Artificial Sequence
<220> FEATURE:
<223> OTHER INFORMATION: SC5 promoter reverse primer

<400> SEQUENCE: 46
agaaagctgg gttgtgacgt ggcagtctga ca                                     32

<210> SEQ ID NO 47
<211> LENGTH: 32
<212> TYPE: DNA
<213> ORGANISM: Artificial Sequence
<220> FEATURE:
<223> OTHER INFORMATION: SC7 promoter forward primer

<400> SEQUENCE: 47
aaaaagcagg ctgtcgaact caccgtgcac ta                                     32

<210> SEQ ID NO 48
<211> LENGTH: 34
<212> TYPE: DNA
<213> ORGANISM: Artificial Sequence
<220> FEATURE:
<223> OTHER INFORMATION: SC7 promoter reverse primer

<400> SEQUENCE: 48
agaaagctgg gttggatgct gctctcttct tctc                                   34

<210> SEQ ID NO 49
<211> LENGTH: 29
<212> TYPE: DNA
<213> ORGANISM: Artificial Sequence
<220> FEATURE:
<223> OTHER INFORMATION: attB1 adaptor primer

<400> SEQUENCE: 49
ggggacaagt ttgtacaaaa aagcaggct                                         29

<210> SEQ ID NO 50
<211> LENGTH: 29
<212> TYPE: DNA
<213> ORGANISM: Artificial Sequence
```

```
<220> FEATURE:
<223> OTHER INFORMATION: attB1 adaptor primer

<400> SEQUENCE: 50
ggggaccact tgtacaaga aagctgggt                                          29

<210> SEQ ID NO 51
<211> LENGTH: 21
<212> TYPE: DNA
<213> ORGANISM: Artificial Sequence
<220> FEATURE:
<223> OTHER INFORMATION: GFP forward primer

<400> SEQUENCE: 51
cagcacgact tcttcaagtc c                                                 21

<210> SEQ ID NO 52
<211> LENGTH: 21
<212> TYPE: DNA
<213> ORGANISM: Artificial Sequence
<220> FEATURE:
<223> OTHER INFORMATION: GFP reverse primer

<400> SEQUENCE: 52
cttcagctcg atgcggttca c                                                 21

<210> SEQ ID NO 53
<211> LENGTH: 20
<212> TYPE: DNA
<213> ORGANISM: Artificial Sequence
<220> FEATURE:
<223> OTHER INFORMATION: OsUbi forward primer

<400> SEQUENCE: 53
atggagctgc tgctgttcta                                                   20

<210> SEQ ID NO 54
<211> LENGTH: 20
<212> TYPE: DNA
<213> ORGANISM: Artificial Sequence
<220> FEATURE:
<223> OTHER INFORMATION: OsUbi reverse primer

<400> SEQUENCE: 54
ttcttccatg ctgctctacc                                                   20
```

PROMOTERS AND METHODS THEREOF

CROSS REFERENCE TO PRIOR APPLICATIONS

This application claims the benefit of a prior-filed U.S. patent application Ser. No. 13/494,568 (filed on Jun. 12, 2012) under 35 U.S.C. §120, which is a prior-filed U.S. patent application Ser. No. 12/583,623 (filed on Aug. 24, 2009, now issued as U.S. Pat. No. 8,237,018) under 35 U.S.C. §120, which are hereby incorporated by reference in their entireties.

This application includes a Sequence Listing in an ASCII text file that is identified as the file name of 8300005SEQ_CRF_rev.txt, the creation date of Aug. 14, 2015, and the file size of 30,895 bytes, the material of which is incorporated by reference.

BACKGROUND

The present invention generally relates to promoters and methods of use and fabrication thereof, and particularly to a promoter used to express a gene, a vector including a promoter, a method of producing a target protein, a method of producing a transformed cell and/or a plant, a transformed plant, a transformed seed, a transformed cell, and PCR primers for a promoter.

A promoter may relate to a genomic region located upstream of a structural gene and may function in the transcription of a structural gene, for example, into mRNA. A promoter may be activated by binding of general transcription factors, and may include base sequences such as a TATA box and/or CAT box which may assist to regulate gene expression. For example, promoters linked to genes may be constitutively activated by general transcription factors to express genes associated with proteins needed for the basal metabolism of a living organism and which may be required in cells at a given concentration. Promoters may also be activated when proteins are needed which are not ordinarily present or only required under special circumstances. For example, inducible promoters may be activated by binding of specific transcription factors, which may be activated in an organism's developmental processes or by external stimuli resulting from surrounding environmental factors.

A foreign gene (i.e., transgene) introduced into a plant, forming a plant having novel characteristics which may develop an agricultural field, may be influenced by transcriptional, post-transcriptional, translational and post-translational elements. A promoter may belong to a transcriptional element and may directly influence transcription of a transgene, for example, to change the expression level of a transgene. A promoter may be the most important factor to change the expression stage or the tissue and/or cell specificity of a transgene.

Although promoters have been isolated from plants to express a transgene, only a few promoters may be practical for use in the transformation of plants. For example, a CaMV (cauliflower mosaic virus) 35S promoter and its derivatives may induce expression of genes in plant tissues and exhibit high activity, for example in vascular tissues and root/leave cells. However, a CaMV 35S promoter has relatively less activity in monocot plants, such as a rice plant, and does not exhibit any activity in certain cells, such as pollen.

Promoters from dicot plants which have been investigated for the transformation of monocot plants have exhibited relatively lower activity compared to promoters originating from monocot plants. A rbcS (ribulose bisphosphate carboxylase/oxygenase small subunit) promoter of rice, a Act1 (actin1) promoter of rice, and a Ubi1 promoter of maize are examples of promoters from monocot plants which have been investigated in the transformation of monocot plants. While Act1 and Ubi1 promoters exhibit a relatively high activity in monocot plants compared to a CaMV 35S promoter, there are drawbacks. For example, the Act1 promoter exhibits activity mainly in vegetative tissue and reproductive tissue, and thus is not effective for expression of a ubiquitous gene in monocot plants. Although the Ubi1 promoter exhibits activity in numerous types of cells, it does not exhibit activity in the substantially all tissues of a plant. Also, while the Ubi1 promoter exhibits a strong activity, especially in young roots, the activity is greatly reduced over time, for example as the root grows.

Accordingly, there is a need for developing a promoter exhibiting a strong, stable and ubiquitous activity in the transformation of plants, including monocot plants. There is a need for suitable promoters useful in the substantially uniform expression of a gene in substantially all the tissues of a plant. There is a need for suitable promoters useful in the production of transformed compositions, and suitable methods for fabricating the same. There is also a need for suitable primers for a variety of novel promoters.

SUMMARY

Embodiments relate to a promoter. In example embodiments, a promoter may include at least one of SEQ ID NO: 1, SEQ ID NO: 2, SEQ ID NO: 3, SEQ ID NO: 4, SEQ ID NO: 5, SEQ ID NO: 6, SEQ ID NO: 7 and SEQ ID NO: 8 (i.e., SEQ ID NO: 1 through SEQ ID NO: 8).

Embodiments relate to a promoter that may be a constitutive expression promoter which is linked to a gene to transform a plant, such as a monocot plant. In example embodiments, a monocot plant may include at least one of a rice, barley, wheat, maize, millet and Indian millet. In embodiments, a promoter may express a gene substantially uniformly in substantially all organs and/or tissues of a plant.

Embodiments relate to a promoter that may include a base sequence complementary to the entire length at least one of SEQ ID NO: 1 through SEQ ID NO: 8. In embodiments, a promoter may include a variant of at least one of SEQ ID NO: 1 through SEQ ID NO: 8. In embodiments, a promoter may include a base sequence complementary to the variant of at least one of SEQ ID NO: 1 through SEQ ID NO: 8.

Embodiments relate to a vector. In example embodiments, a vector may include a promoter consisting of at least one of SEQ ID NO: 1 through SEQ ID NO: 8. In embodiments, a vector may be a recombinant plant expression vector and the promoter may be a constitutive promoter. In embodiments, a target gene downstream of a promoter encoding a target protein may be operably linked. In embodiments, a promoter of a vector may express a gene substantially uniformly in substantially all organs and/or tissues of a plant. In embodiments, a vector may include a variant of at least one of SEQ ID NO: 1 through SEQ ID NO: 8.

Embodiments relate to a transformed plant. In example embodiments, a plant may include a promoter consisting of at least one of SEQ ID NO: 1 through SEQ ID NO: 8. Embodiments relate to a transformed seed. In example embodiments, a seed may include a promoter consisting of at least one of SEQ ID NO: 1 through SEQ ID NO: 20. Embodiments relate to a transformed cell. In example embodiments, a cell may include a promoter consisting of at least one of SEQ ID NO: 1 through SEQ ID NO: 20.

Embodiments relate to a method of forming a target protein. In embodiments, a plant may be transformed using a vector that may include a promoter which may include at least one of SEQ ID NO: 1 through SEQ ID NO: 8. In example embodiments, a target protein may include at least one of interleukin, interferon, platelet-derived growth factor, hemoglobin, elastin, collagen, insulin, fibroblast growth factor, human growth factor, human serum albumin and erythropoietin.

Embodiments relate to a method of transforming a cell and/or plant. In embodiments, a plant cell may be transformed using a vector that may include a promoter which may include at least one of SEQ ID NO: 1 through SEQ ID NO: 8. In example embodiments, a transformed plant may be redifferentiated from a transformed plant cell.

DRAWINGS

The patent or application file contains at least one drawing executed in color. Copies of this patent or patent application publication with color drawing(s) will be provided by the Office upon request and payment of the necessary fee.

DESCRIPTION

Figure 1:
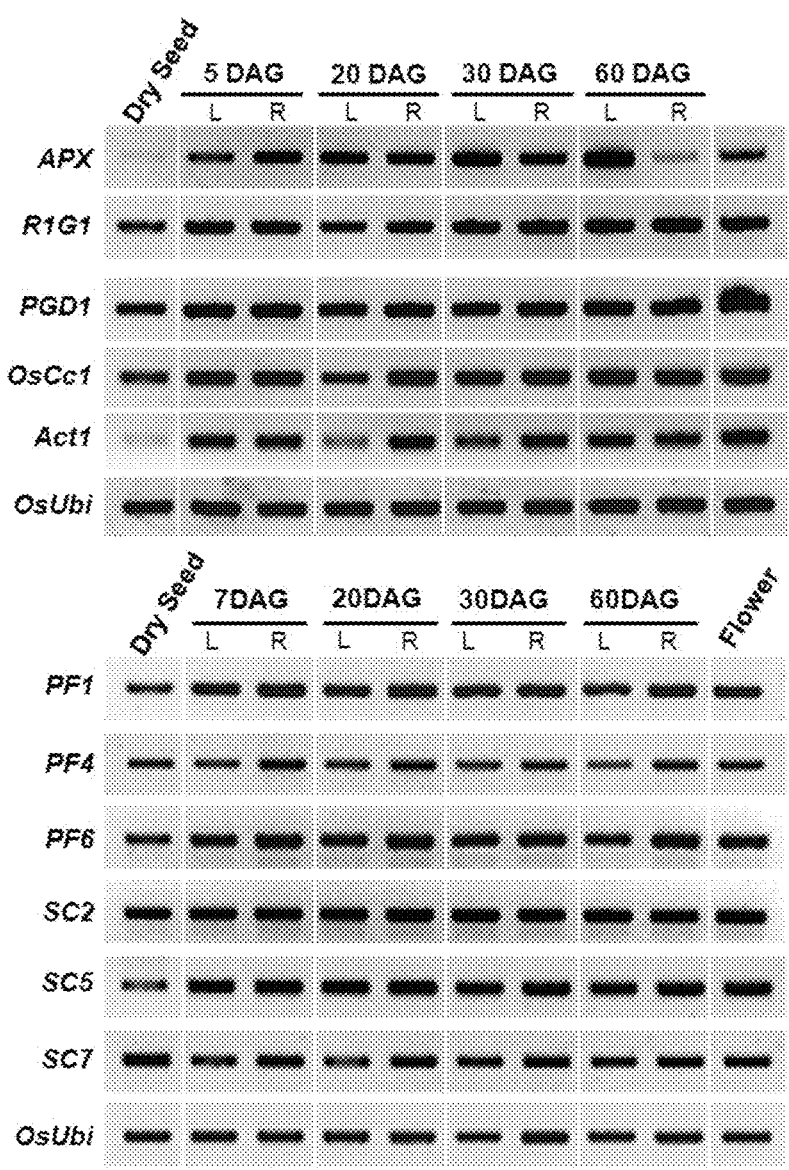
FIG. 1 shows the expression of genes according to embodiments relative to constitutive expression genes (OsCc1, Act1 and Ub1) in various tissues of a plant.

Embodiments relate to a promoter derived from monocot plants, such as rice. In embodiments, the promoter may be suitable for the transformation of plants including monocot plants and may be suitable for the constitutive expression of plant genes. A promoter according to embodiments may express a gene substantially uniformly in substantially all the organs and/or tissues of a plant. In embodiments, a promoter may include at least one of SEQ ID NO: 1 through SEQ ID NO: 8 and may include a base sequence complementary to the entire length of SEQ ID NO: 1 to SEQ ID NO: 8. "Complementary" may relate to hybridization and/or base pairing between nucleotides or nucleic acids, for instance, between two strands of a DNA molecule.

A promoter may relate to a DNA molecule to which RNA polymerase binds in order to initiate transcription and may refer to a DNA region upstream of a structural gene. A plant promoter may relate to a promoter which may initiate transcription in a plant cell. A constitutive promoter may relate to a promoter which may be active in most environmental conditions and/or development states and/or cell differentiation states. Since the selection of a transformant may be carried out by various tissues at various stages, a constitutive promoter may be preferable. However, one is not limited to selecting a constitutive promoter according to embodiments.

In embodiments, a promoter may include at least one of an ascorbate peroxidase (APX) promoter of SEQ ID NO: 1, a putative R1G1 domain containing protein (R1G1) promoter of SEQ ID NO: 2, a PF1 promoter (60S acidic ribosomal protein P1) of SEQ ID NO: 3, a PF4 promoter (40S ribosomal protein S8) of SEQ ID NO: 4, a PF6 promoter (ribosomal protein S26E family protein of SEQ ID NO: 5, an SC2 promoter (histone H3.3) of SEQ ID NO: 6, an SC5 promoter (60S ribosomal protein L9) of SEQ ID NO: 7, and an SC7 promoter (histone H2B.1) of SEQ ID NO: 8.

In embodiments, a promoter may include at least one of SEQ ID NO: 1 through SEQ ID NO: 8 and may be operatively linked to a gene to transform a plant, including a monocot plant. In embodiments, a monocot plant may be, but is not limited to, at least one of a rice, barley, wheat, maize, millet and Indian millet. In embodiments, a promoter may express a gene substantially uniformly in substantially all the organs and/or tissues of a plant, including a monocot plant.

Embodiments relate to variants of a promoter which may include a variant of at least one of SEQ ID NO: 1 through SEQ ID NO: 8. In embodiments, a variant may have different base sequences but include functional characteristics similar to those of at least one of SEQ ID NO: 1 through SEQ ID NO: 8. A variant may result from at least one of a substitution, deletion and insertion of nucleic acid base(s), or combinations thereof, including functional fragments thereof. In example embodiments, a base sequence complementary to the variant at least one of SEQ ID NO: 1 through SEQ ID NO: 8 may be included.

In example embodiments, a variant of a promoter may have a sequence identity of at least 70%, preferably at least 80%, even more preferably 90%, and most preferably at least 95% to the at least one of SEQ ID NO: 1 through SEQ ID NO: 8. A percentage of sequence identity to a polynucleotide may be determined by comparing two optimally aligned sequences over a comparison window, wherein the portion of the polynucleotide sequence in the comparison window may include additions or deletions (i.e., gaps) and/or substitutions as compared to the reference sequence (which does not include additions, deletions or substitutions) for optimal alignment of the two sequences.

Substantial identity of polynucleotide sequences may relate to a polynucleotide including a sequence having between 50-100% sequence identity, preferably at least 70% sequence identity, preferably at least 80% sequence identity, more preferably at least 90%, and most preferably at least 95%. Substantial identity may also relate to when two nucleotide molecules are hybridized specifically to each other under a stringent condition such that their sequences may be substantially identical to each other. For example, stringent condition may vary depending on nucleotide sequences, and thus can be different at a different condition.

At certain ionic strength and pH, for example, a stringent condition may be selected to have a temperature that is about 10° C. lower than the heat-melting point (Tm) of a specific sequence. Tm may relate to a temperature at which 50% of a target sequence is hybridized to a fully complementary probe (under the condition of certain ionic strength and pH). For example, a stringent condition for carrying out Southern blot analysis may include washing with 0.2×SSC at 65° C. For an oligonucleotide probe, washing may be carried out with 6×SSC at 42° C.

Embodiments relate to a vector. A vector may relate to a DNA fragment(s) and/or nucleotide molecules delivered to a cell. A vector may replicate DNA and be independently reproduced in a host cell. The terms "delivery system" and "vector" may be interchangeably used. An expression vector may relate to a recombinant DNA molecule including a desired coding sequence and other appropriate nucleotide sequences that are essential for the expression of a coding sequence in a specific host organism, such an operatively-linked coding sequence. The aforementioned other appropriate sequences may include at least one of an promoter, an enhancer, a terminator and a polyadenylation signal that may be suitable for use in a eukaryotic cell. For example, any related terminator may be used according to embodiments. Examples thereof include, but are not limited to, nopaline synthase (NOS), rice α-amylase RAmyl A terminator, phaseoline terminator, and a terminator for optopine gene of *Agrobacterium tumefaciens*. Since a terminator region may increase the reliability and efficiency of transcription in plant cells, a terminator may be highly preferable.

"Recombinant" may relate to a cell which replicates a heterogeneous nucleotide and/or expresses the nucleotide, a peptide, a heterogeneous peptide, or a protein encoded by a heterogeneous nucleotide. A recombinant cell may express a gene or a gene fragment in a sense or antisense form, which are not found in the natural state of the cell. Embodiments relate to a vector which may be a recombinant vector.

Embodiments relating to vectors which may be used to introduce DNA into a plant host may include viral vectors, for example, non-integrative plant viral vectors, such as derivable from the double stranded plant viruses (for example, CaMV) and single stranded viruses, gemini viruses and the like. The use of such vectors may be preferable, particularly when it is difficult to stably transform a plant host.

Embodiments relating to vectors may preferably include at least one selective marker. A selective marker may relate to a nucleotide sequence having a property which allows selection based on a common chemical method. It may be any kind of gene that may be used for the differentiation of transformed cells from non-transformed cell. Examples thereof include, but are not limited to, herbicide-resistant genes, such as glyphosate or phosphintricin, and antibiotic-resistant genes, such as kanamycin, G418, bleomycin, hygromycin or chloramphenicol.

In example embodiments, a recombinant plant expression vector may include a Ti-plasmid vector that, when present in a suitable host, such as *Agrobacterium tumefaciens*, is capable of transferring part of itself, the so-called T-region, to a plant cell. Embodiments include different types of Ti-plasmid vectors, for example those disclosed in EP 0 116 718, to transfer chimeric DNA sequences into plant cells, or protoplasts, from which new plants may be generated which stably incorporate said chimeric DNA in their genomes. Particularly preferred forms of Ti-plasmid vectors are the so-called binary vectors as described in EP No. 0 120 516 B1 and U.S. Pat. No. 4,940,838.

In embodiments, a vector may be a recombinant plant expression vector including a promoter in accordance with embodiments. An example of the recombinant plant expression vector may be, but is not limited to, a vector shown in FIG. 2. As shown in the example embodiment of FIG. 2, a modified green fluorescent protein (GFP), a protease inhibitor II terminator gene ($T_{PINII}$), an OsCc1 promoter (Pcytc), a herbicide-resistant gene Bar (phosphinotricine acetyltransferase gene) and a nopaline synthase terminator ($T_{NOS}$) may be operably linked to a promoter according to embodiments. Also as shown in the example embodiment of FIG. 2, a MAR sequence may be attached to the terminal of the right-border sequence. In embodiments, the aforementioned attachment may minimize the change in expression in the chromosome in various sites of the chromosome such that only the inherent activity of the promoter according to embodiments can be measured.

In embodiments a vector, such as recombinant plant expression vector, may be prepared by operably linking a target gene encoding a target protein downstream of a promoter according to embodiments. "Operably linked" may relate to the element of an expression cassette which functions as a unit to express, for example, a heterogeneous protein. In example embodiments, a promoter that may be operably linked to a heterogeneous DNA which may encode a protein may promote the production of functional mRNA corresponding to the heterogeneous DNA.

In embodiments, a target protein may be any kind of protein, and examples thereof include, but are not limited to, proteins having medical utility, such as enzymes, hormones, antibodies or cytokines, and proteins which can accumulate large amounts of nutrients capable of improving the health of animals including humans. Example embodiments of a target protein include, but are not limited to, interleukin, interferon, platelet-derived growth factor, hemoglobin, elastin, collagen, insulin, fibroblast growth factor, human growth factor, human serum albumin and erythropoietin.

Embodiments relate to a method of producing a target protein. In embodiments, the target protein may be produced by transforming a plant using a vector including a promoter in accordance with embodiments. In example embodiments, the target protein may be produced by constitutive expression in a plant and may include transforming a plant with a recombinant plant expression vector. Embodiments of a target protein are described hereinabove.

According to embodiments, plant transformation may refer to any method of introducing DNA is into a plant. Such transformation methods do not necessarily have a period for regeneration and/or tissue culture. In embodiments, transformation of a plant species is possible for dicot plants and for monocot plants. In embodiments, any transformation method can be used to introduce a hybrid DNA according to embodiments to a suitable ancestor cells. Example methods include a calcium/polyethylene glycol method for protoplast transformation, electroporation of protoplasts, microinjection into plant material, (DNA or RNA-coated) particle bombardment of various plant materials, gene gun methods, infection with (non-integrative) viruses, in planta *Agrobacterium tumefaciens*-mediated gene transfer by infiltration of adult plants or transformation of mature pollen or microspores (EP 0 301 316) and the like. A preferred method according to embodiments may include *Agrobacterium*-mediated DNA transfer. More preferably, use of a so-called binary vector technology, disclosed in EP A 120 516 and U.S. Pat. No. 4,940,838, may be used.

According to embodiments, a plant cell that may be used in plant transformation may be any plant cell. A plant cell may be a cultured cell, a cultured tissue, a cultured organ or a whole plant, and may preferably be a cultured cell, a cultured tissue or a cultured organ, and most preferably a cultured cell according to embodiments. Plant tissue may relate to a differentiated or undifferentiated plant tissue. Embodiments of a plant tissue include, but are not limited to, root, stem, leaf, pollen, seed, cancerous tissue, and cells of various shapes that are used in culture, namely, single cells, protoplasts, buds and callus tissues. In embodiments, a plant tissue may be in planta or in organ culture, tissue culture or cell culture.

Embodiments relate to a method of producing a transformed cell and/or plant. In embodiments, the method may include transforming a plant cell with a vector including a promoter according to embodiments, and may include differentiating a transformed plant from a transformed plant cell. In example embodiments, a recombinant plant expression vector may be used. In example embodiments, the plant transformation may be mediated by, for example, *Agrobacterium tumefaciens*. In example embodiments, redifferentiation of the transformed plant from the transformed plant cell may be carried out using any related method in the art.

Embodiments relate to a transformed plant, which may be produced by the above-described method. The plant may preferably be, but is not limited to, a monocot plant, and more preferably may be rice, barley, wheat, maize, millet or Indian millet. Embodiments relate to a transformed seed. In embodiments, the transformed seed may be obtained from a transformed plant. A seed preferably may be derived from, but is not limited to, a monocot plant, and more preferably may be from rice, barley, wheat, maize, millet or Indian millet. Embodiments relate to a transformed cell. In embodiments, the transformed cell may be obtained from a transformed plant. A cell preferably may be derived from, but is not limited to, a monocot plant, and more preferably may be from rice, barley, wheat, maize, millet or Indian millet.

Hereinafter, the present invention will be described in further detail with reference to example embodiments. It is to be understood, however, that these examples are for illustrative purposes only and are not to be construed to limit the scope of the present invention.

1. Embodiment of Selection and Extraction of Promoter Sequences.

Using the rice genome sequences of the international rice genome sequencing project (IRGSP), which was established in 1997 and completed the sequencing of the rice genome in December, 2004, and gene annotation data from the Institute for Genomic Research (TIGR) which carried out gene annotation based on the rice genome sequences, a region was selected to investigate its activity in a transformation, for example its activity in a vector. An annotated bacterial artificial chromosome (BAC) was selected, and about 2 kbp of sequence upstream from a ATG start codon of a coding sequence (CDS) was selected to be investigated as a promoter region. Only the 2-kbp sequence was extracted, separately, and used as a template for constructing PCR primers for isolating about 1.7-2-kb promoters from the 2-kbp sequence.

2. Embodiment of Analysis of a Constitutive Expression Gene by RT-PCR.

For the analysis of a constitutive expression gene, samples were collected from seeds and leaf, root and flower tissues of 5-day-old (or 7-day-old), 20-day-old, 30-day-old and 60-day-old seedlings. For the preparation of the samples, the seeds were disinfected with about 70% ethanol and about 20% chlorax solutions, grown in a dark condition for about 5 days, and then developed in a greenhouse. To extract the total RNA, an RNeasy plant mini-kit (Qiagen, Cat. No. 74904) was used. A first-strand cDNA was synthesized using about 400 ng of the extracted total RNA (Invitrogen, Cat. No. 18080-051), and PCR was performed using about 1 µl of the synthesized cDNA product as a template. The primers used in the PCR reaction were as follows, and an ubiquitin (Ubi) primer set was used as a cDNA loading control.

```
Forward primer APX:
5'- GACCTCTAGACCGCCGTATT-3'      (SEQ ID NO: 9)

Reverse primer APX:
5'- GCCAACCACTCGCAATCCAA-3'      (SEQ ID NO: 10)

Forward primer R1G1:
5'- CTTCTCGATTGCCGTGTGCT-3'      (SEQ ID NO: 11)

Reverse primer R1G1:
5'- GCAAGTCTCAAGCTCTCAAT-3'      (SEQ ID NO: 12)

Forward primer PF1:
5'- GGTCTCTTCGCCAAGCTCCT-3'      (SEQ ID NO: 13)

Reverse primer PF1:
5'- CGCCTCCTCCTTCTTCTCCT-3'      (SEQ ID NO: 14)

Forward primer PF4:
5'- CAATGTGGCAGAGCTGATGG-3'      (SEQ ID NO: 15)

Reverse primer PF4:
5'- GGTCTGTAGGCACGACATAG-3'      (SEQ ID NO: 16)

Forward primer PF6:
5'- GAAGCTGTACGCCAAGGT-3'        (SEQ ID NO: 17)

Reverse primer PF6:
5'- TAGGTGCGAGCAACATTAGG-3'      (SEQ ID NO: 18)

Forward primer SC2:
5'- CTGCGGAGGCATACCTTGTT-3'      (SEQ ID NO: 19)

Reverse primer SC2:
5'- ACACTACGACGCATGCTTCA-3'      (SEQ ID NO: 20)

Forward primer SC5:
5'- CATCTTGCGGTCGGAGAA-3'        SEQ ID NO: 21)

Reverse primer SC5:
5'- TACGCATCCTCTGTGATGGT-3'      (SEQ ID NO: 22)

Forward primer SC7:
5'- CGTCACCAAGTTCACTTC-3'        (SEQ ID NO: 23)

Reverse primer SC7:
5'- CCACCTAATTCTTCTTACAGTC-3'    SEQ ID NO: 24)

Forward primer PGD1:
5'- CCGTGAGCTAGCGAGGATCT-3'      (SEQ ID NO: 25)

Reverse primer PGD1:
5'- CCGGTAGGAGTCGAAGTACG -3'     (SEQ ID NO: 26)

Forward primer OsCc1:
5'- ACTCTACGGCCAACAAGAAC-3'      (SAEQ ID NO: 27)

Reverse primer OsCc1:
5'- CTCCTGTGGCTTCTTCAACC-3'      (SEQ ID NO: 28)

Forward primer Act1:
5'- ATGGTGTCAGCCACACTGTC-3'      (SEQ ID NO: 29)

Reverse primer Act1:
5'- TAACCACGCTCCGTCAGGAT-3'      (SEQ ID NO: 30)

Forward primer OsUbi:
5'- ATGGAGCTGCTGCTGTTCTA-3'      (SEQ ID NO: 31)

Reverse primer OsUbi:
5'- TTCTTCCATGCTGCTCTACC-3'      (SEQ ID NO: 32)
```

The PCR reaction was performed in a PTC 200 PCR machine (MJ research) using about 1 µl of cDNA, 2× Taq premix (Solgent. Co. Cat. No. EP051020-T2B6-1), about 4 pmol of each template-specific primer in a total reaction volume of about 20 µl for about 32 cycles, each consisting of about 95° C. for about 30 sec, about 55° C. for about 30 sec and about 72° C. for about 1 min.

3. Embodiments of Amplification and Isolation of Promoters.

Using the isolated 2-kbp promoter sequence as a template and a primer designer 4 program (ver.4.20, Scientific & Educational software), PCR primers for isolating about 1.8-2-kb promoters were designed. The design conditions were as follows: the GC content of PCR primers: about 40-60%, Tm: about 55-65° C., and the concentrations of salt and free Mg: about 0 and about 0.15 mM, respectively. The primers (PCR primers) were designed such that the template-specific region was about 20 bp in length and the 5' adaptor sequence was about 12 bp in length. The adaptor sequence was inserted for site-specific recombination other than existing cloning methods which are performed using restriction enzymes and DNA ligase. DNA used as a template was obtained by seeding a *Japonica* type Nipponbare cultivar rice, growing the plant in a greenhouse for about 3 weeks, cutting only the leap portion from the plant, and extracting genomic DNA from the leaf. The genomic DNA was obtained by freezing the cut leaf rapidly with liquid nitrogen, crushing the frozen leaf finely with a mortar and pestle, and then isolating the genomic DNA from the crushed leaf using DNAzol solution (molecular research center, Cat. No. DN128). The first reaction was carried out to isolate a specific promoter from the rice genome and performed using 32-bp template-specific primers linked with a 12-bp adaptor sequence. The primer sequences were as follows:

```
Forward template-specific primer:
5'-AAAAAGCAGGCT-tempate specific sequence-3'

Reverse template-specific primer:
5'-AGAAAGCTGGGT-template specific sequence-3'
```

Embodiments of gene-specific primer sequences were as follows:

a. APX promoter primers

```
Forward primer:
                                      (SEQ ID NO: 33)
5'-AAAAAGCAGGCTgtaaggtgacatggcatatc-3'

Reverse primer:
                                      (SEQ ID NO: 34)
5'-AGAAAGCTGGGTccaatccgaatcaatcaatc-3'
``` b. R1G1 promoter primers

```
Forward primer:
                                      (SEQ ID NO: 35)
5'-AAAAAGCAGGCTatagctgttgtactgatgtc-3'

Reverse primer:
                                      (SEQ ID NO: 36)
5'-AGAAAGCTGGGTtctctcgcagtattaccaac-3'
``` c. PF1 promoter primers

```
Forward primer:
                                      (SEQ ID NO: 37)
5'-AAAAAGCAGGCTctcggtgaagatagagaagg-3'
```

```
Reverse primer:
                                      (SEQ ID NO: 38)
5'-AGAAAGCTGGGTctcgagctgatctacgaact-3'
``` d. PF4 promoter primers

```
Forward primer:
                                      (SEQ ID NO: 39)
5'-AAAAAGCAGGCTtctggcatcgatatgctcct-3'

Reverse primer:
                                      (SEQ ID NO: 40)
5'-AGAAAGCTGGGTtggagtcacgcgagatacct-3'
``` e. PF6 promoter primers

```
Forward primer:
                                      (SEQ ID NO: 41)
5'-AAAAAGCAGGCTggaccaaccgaagtccttcc-3'

Reverse primer:
                                      (SEQ ID NO: 42)
5'-AGAAAGCTGGGTtcctgcgcttgaaggtct-3'
``` f. SC2 promoter primers

```
Forward primer:
                                      (SEQ ID NO: 43)
5'-AAAAAGCAGGCTttacgtatagccttttcctt-3'

Reverse primer:
                                      (SEQ ID NO: 44)
5'-AGAAAGCTGGGTgacagaatatgctgtgacaa-3'
``` g. SC5 promoter primers

```
Forward primer:
                                      (SEQ ID NO: 45)
5'-AAAAAGCAGGCTtcctcttgccccttcctcgg-3'

Reverse primer:
                                      (SEQ ID NO: 46)
5'-AGAAAGCTGGGTtgtgacgtggcagtctgaca-3'
``` h. SC7 promoter primers

```
Forward primer:
                                      (SEQ ID NO: 47)
5'-AAAAAGCAGGCTgtcgaactcaccgtgcacta-3'

Reverse primer:
                                      (SEQ ID NO: 48)
5'-AGAAAGCTGGGTtggatgctgctctcttcttctc-3'
```

A first PCR reaction was carried out using about 50 ng of genomic DNA, 2× Taq premix (Solgent. Co. Cat. No. EP051020-T2B6-1) and about 10 pmol of each template-specific primer in a total reaction volume of about 50 µl for about 30 cycles, each consisting of about 95° C. for about 1 min, about 55° C. for about 1 min and about 68° C. for about 2 min.

A second PCR reaction was carried out to insert and amplify a specific adaptor sequence (att site) which may be used to insert a promoter into a transformation vector. The length of the sequence to be additionally inserted into the promoter was about 29 bp. To increase the efficiency of PCR, only a portion (12 bp) of the sequence was attached to the template-specific sequence by overhang and subjected to the first PCR reaction. Then, about 1/50 (1 µl) of the PCR reaction solution was taken and subjected to the second PCR reaction using primers (adaptor sequence primers) having full-length recombinant sequences. Thus, the PCR product had all the att sequences for recombination with the promoter. The adaptor primer sequences were as follows:

```
attB1 adaptor primer:
                                    (SEQ ID NO: 49)
5'-GGGGACAAGTTTGTACAAAAAAGCAGGCT-3' attB2 adaptor primer:
                                    (SEQ ID NO: 50)
5'-GGGGACCACTTTGTACAAGAAAGCTGGGT-3'
```

The second PCR reaction was carried out using about 1 µl of the first PCR product, 2× Taq premix (Solgent. Co. Cat. No. EP051020-T2B6-1) and about 2 pmol of each adaptor primer in a total reaction volume of about 50 µl for about 5 cycles, each consisting of about 95° C. for about 30 sec, about 45° C. for about 30 sec and about 68° C. for about 2 min, followed by about 20 cycles, each consisting of about 95° C. for about 30 sec, about 55° C. for about 30 sec and about 68° C. for about 2 min. The PCR reactions were carried out using a Gateway system (Invitrogen, Cat. No. 12535-029) according to the method suggested by Invitrogen.

4. Embodiments of Cloning of Amplified Promoters.

The promoter was inserted into a vector using a Gateway system (Invitrogen, Cat. No. 12535-029). The amplified promoter was electrophoresed on about 1% agrose gel, separated into bands on the gel and purified using the Mega-spin agarose gel extraction kit (Intron, Cat. No. 17183). A BP reaction was carried out using about 5 µl of the purified promoter, about 4 µl of a BP clonase enzyme mixture, about 4 µl of 5×BP reaction buffer, about 300 ng/2 µl of a pDONR vector, and TE buffer (about 10 mM Tris/pH about 8.0, about 1 mM EDTA) in a total reaction volume of about 20 µl at about 25° C. for about 16 hours. Then, about 6 µl of an LR clonase enzyme mixture, about 1 µl of about 0.75 M NaCl and about 450 ng/3 µl of a transformation vector were added to the reaction product and subjected to an LR reaction in a total reaction volume of about 30 µl at about 25° C. for about 8 hours. About 3 µl of proteinase was added thereto and allowed to react at about 37° C. for about 1 hour, and then about 2 µl of the reaction product was taken and transformed into DH5α competent cells. The transformed DH5α cells were plated in LB agar medium containing about 50 µg/ml of a Spectinomycin antibiotic and were grown in an incubator at about 37° C. for about 12 hours. DNA was extracted from the selected cells, and whether the promoter has been inserted into the extracted DNA was confirmed by PCR. Then, the DNA was subjected to sequencing and BLASTN analysis to confirm complete insertion of the isolated promoter.

A vector (pMJ401) is described as follows. Between the right-border sequence and the left-border sequence, a cassette to be replaced with a promoter according to embodiments subsequent to recombination is linked with the visible marker gene GFP and a protease inhibitor II at the 3' end. The cassette has the att sequences to facilitate BP and LR reactions. The selection gene (selection marker gene) was prepared such that the herbicide-resistant gene bar (phosphinotricine acetyltransferase gene) was controlled by the constitutive expression promoter OsCc1 (see U.S. Pat. No. 6,958,434). The gene was linked with a nopalin synthase (NOS) terminator. Also, a MAR sequence was attached to the terminal of the right-border sequence to minimize the change in expression in various sites of the chromosome, such that only the inherent activity of the promoter could be measured.

5. Embodiments of *Agrobacterium*-Mediated Transformation of Rice.

About 70% (v/v) ethanol was added to T0 hulled rice seeds (*Oryza sativa* L. cv *Nakdong*) and gently mixed for about 1 minute to wash the seeds. The washed seeds were sterilized by treatment in about 20% chlorax for about 1 hour and washed several times with sterile water. For transformation, the washed rice seeds were incubated on a callus induction medium (2N6) for about one month according to the method of Jang et al (Jang, I-C. et al., Mol breeding, 5:453-461, 1999) to induce embryonic callus, and then were co-cultivated with *Agrobacterium* obtained by an *Agrobacterium* triple mating method so as to insert the promoter-inserted transformation vector into the rice genome. Then, the plant was incubated on a 2N6-CP medium for selecting transformed callus for about one month. The grown cells were selected and cultured in a redifferentiation medium (MS-CP) for about 1-2 months, and a redifferentiated plant was acclimated in a greenhouse. The acclimated T0 rice was treated with the non-selective herbicide basta, and only the plants showing herbicide resistance were selected and subjected to a progeny test.

6. Embodiments of Analysis of Promoter Activity by RT-PCR and Real Time qRT-PCR

For the analysis of promoter activity, total RNA was extracted from the seeds of transformed plants and the leaf, root and flower tissues of 5-day-old, 20-day-old, 30-day-old and 60-day-old seedlings. An RNeasy plant mini-kit (Qiagen, Cat. No. 74904) was used to extract the total RNA from each tissue. A first-strand cDNA was synthesized using about 400 ng of the extracted total RNA (Invitrogen, Cat. No. 18080-051), and PCR was performed using about 1 µl of the synthesized cDNA product as a template. The PCR reaction was performed using two kinds of primer sets. The first primer set was a primer set (primer GFP) for comparing the expression levels of GFP inserted downstream of the promoters, and the second primer set was a primer set (primer Ubi) as a cDNA loading control. The primer sequences were as follows.

```
Forward primer GFP:
5'-CAGCACGACTTCTTCAAGTCC-3'    (SEQ ID NO: 51)

Reverse primer GFP:
5'-CTTCAGCTCGATGCGGTTCAC-3'    (SEQ ID NO: 52)

Forward primer OsUbi:
5'-ATGGAGCTGCTGCTGTTCTA-3'     (SEQ ID NO: 53)

Reverse primer OsUbi:
5'-TTCTTCCATGCTGCTCTACC-3'     (SEQ ID NO: 54)
```

The RT-PCR reaction was carried out in a PTC 200 PCR machine (MJ research) using about 1 µl of cDNA, 2× Taq premix (Solgent. Co. Cat. No. EP051020-T2B6-1) and about 2 pmol of each template-specific primer in a total reaction volume of about 20 µl for about 39 cycles, each consisting of about 95° C. for about 30 sec, about 55° C. for about 30 sec and about 72° C. for about 30 sec.

The real-time qRT-PCR reaction was carried out in Mx3000P (Stratagene) using about 1 µl of cDNA, 2×SYBR green qRT-PCR premix (Invitrogen. Cat. No. 11765-100) and about 2 pmol of each template-specific primer in a total reaction volume of about 20 µl for about 40 cycles, each consisting of about 95° C. for about 15 sec and about 60° C.

for about 30 sec. After completion of the reaction, the promoter activity was quantitatively analyzed using the program Mx3000P (Stratagene) according to the manufacturer's instruction.

7. Embodiments of Observation of GFP Expression and Analysis of Promoter Activity in Each Organ of Rice.

GFP fluorescence in different regions of the leaves and roots of 7 days after germination (DAG) rice plants was visualized and photographed using a confocal laser scanning microscope (Carl Zeiss LSM410 CLSM, Jena, Germany). Pseudo-color, similar to the color observed under a fluorescence microscope, was added to the images by importing data collected in the green and red channels of the confocal microscope. Sections along the optical axis were prepared and projected into a single image. The other regions were observed using a research stereomicroscope (SZX9-3122, Olympus, Tokyo, Japan) equipped with an attachment for fluorescence observations. Images were captured using a C5060-ZOOM digital camera (Olympus). Observations under blue light were carried out using a specific filter set (460-480 nm excitation filters, dichroic mirrors of 485 nm and a 495-540 nm barrier filter).

8. Embodiments of Immunoblotting Analysis

Total soluble proteins were extracted from 30-day-old leaves, roots and flowers. The extraction buffer consisted of 20 mM Tris-Cl, pH 8.0, 10 mM EDTA pH 8.0, 30 mM NaCl and 100 µM phenylmethylsulphonylfluoride (PMSF). The extracts were centrifuged at 9,000 g at 4° C. for 30 min and protein concentrations were determined using the Bradford method (Bio-Rad, Hercules, Calif.). Protein extracts were then separated on 12% SDS polyacrylamide gels and blotted onto a polyvinylidenedifluoride (PVDF) membrane (Immobilon-P, Millipore Co., Billerica, Mass.) using a semi-dry transfer apparatus (Hoefer, Inc., San Francisco, Calif.). The immunoreactive proteins were detected using primary antibodies against GFP (Nacalai Tesque, Inc., Kyoto). The chemiluminescence signals generated by the bound antibodies were detected using the Pierce Super Signal Substrate (Pierce, Rockford, Ill.) according to the manufacturer's protocol. Recombinant GFP proteins were used as a positive control (Abcam, Cambridge, UK).

Example 1

Analysis of Expression of Genes in Each Rice Tissue

To examine the tissue-specific activities of the APX and R1GI promoters, samples were collected from the seeds of the transformed rice and the leaf (L in FIG. 1), root (R in FIG. 1) and flower tissues of 5-day-old (or 7-day-old), 20-day-old, 30-day-old and 60-day-old seedlings, and total RNA was extracted from each sample. cDNA was synthesized using the RNA as a template and amplified by PCR. The PCR products were electrophoresed on about 2% agarose gel.

FIG. 1 shows the results obtained by comparing the expression patterns of eight constitutive expression genes in various tissues of rice using RT-PCR. As can be seen in FIG. 1, APX, R1G1, PF1, PF4, PF6, SC2, SC5 and SC7 genes used in the present invention were expressed substantially uniformly in various tissues of rice. Also, these genes showed expression patterns similar to those of related constitutive expression genes OsCc1 and Act1, suggesting they may be constitutive expression genes.

Example 2

Construction of Rice Transformation Vector and Structure of Promoter

Figure 2:
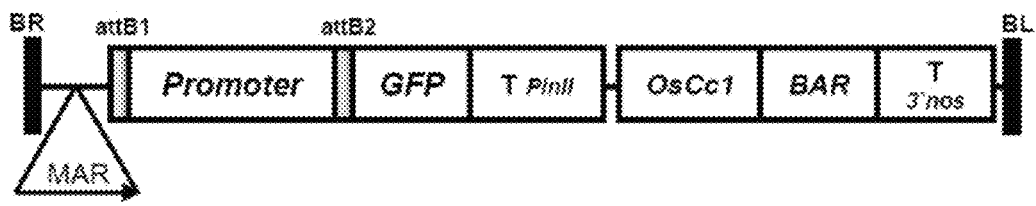
FIG. 2 is a schematic diagram of a vector according to embodiments.

A vector for analyzing promoter activity was constructed and is shown in FIG. 2. FIG. 2 shows a pMJ401 vector. The vector may be a parent vector for cloning the isolated promoter by PCR. The attR1 and attR2 sites are sites where recombination (site-specific recombination) with the attL1 and attL2 sequences of the promoter may occur after a BP reaction. After an LR reaction, a cassette was replaced with the promoter, and the attR1 and attR2 sequences were also replaced with attB1 and attB2 sequences.

Figure 3:
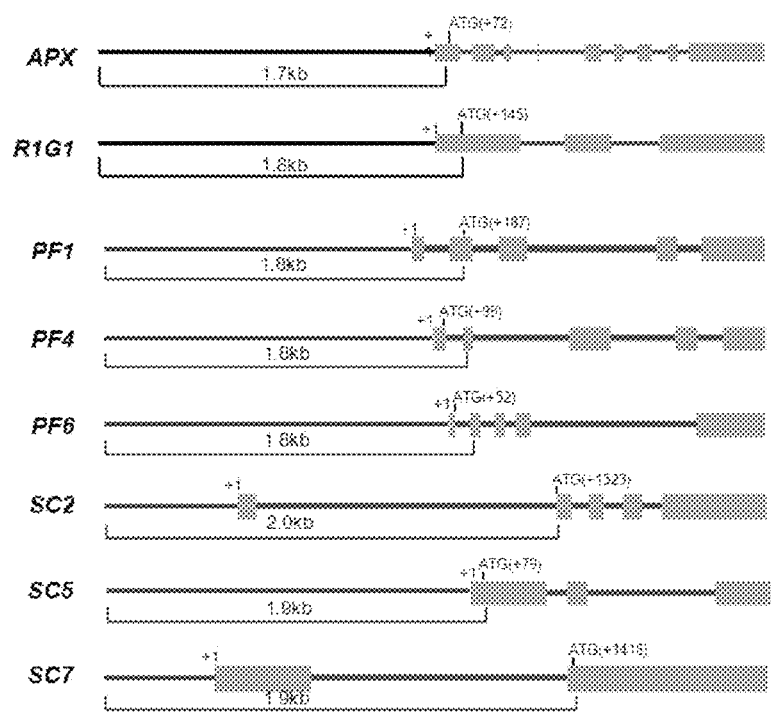
FIG. 3 shows structures of promoters according to embodiments.

A description is provided as follows: MAR: matrix attachment region (1.3 kb), X98408; cassette B: conversion cassette B (1.7 kb; Invitrogen, Cat. No. 11828-019); GFP: modified green fluorescent protein gene (0.74 kb), U84737; TPINII: protease inhibitor II terminator (1.0 kb), X04118; OsCc1: cytochrome c promoter (0.92 kb), Af399666; BAR: phosphinotricine acetyltransferase gene (0.59 kb), X17220; and TNOS: nopaline synthase terminator (0.28 kb). FIG. 3 shows the structures of embodiments of promoters disposed in a rice genome.

Example 3

Figure 4:
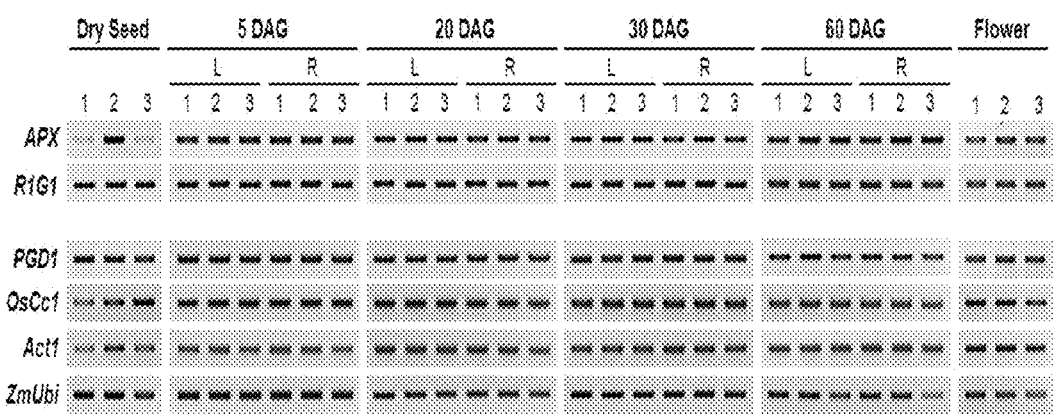
FIG. 4 shows results obtained by observing the expression levels of Green Fluorescent Protein (GFP) in seeds of transformed plant according to embodiments as well as the leaf and root tissues of 5-day-old, 20-day-old and 30-day-old the plants.

Analysis of Promoter Activity (e.g., GFP Expression Level) in Each Tissue of Transformed Rice by RT-PCR RNA was extracted from the seeds of the transformed rice and the leaf, root and flower tissues of 5-day-old, 20-day-old, 30-day-old and 60-day-old seedlings. cDNA was synthesized using the RNA as a template and amplified by PCR. The PCR products were electrophoresed on about 2% agarose gel. Each PCR product was loaded in an amount of about 5 µl. FIG. 4 shows the results obtained by semi-quantitatively analyzing the GFP expression level caused by each promoter in the rice seeds and the leaf (L), root (R) and flower tissues of 5-day-old, 20-day-old, 30-day-old and 60-day-old seedlings using RT-PCR. GFP was a PCR product amplified with GFP primers and was used to compare the expression levels of the GFP gene inserted downstream of the promoters. The PCR product was 141 bp in size. In view of the difference in gene expression according to the variation between events, the analysis of the transformants for each promoter was carried out using 3 events having different promoter insertion sites.

FIG. 4 illustrated that, for example, APX and R1G1 promoters were novel promoters, which showed gene expression levels similar to or lower than those of the related PGD1 promoter, OsCc1 promoter, Act1 promoter and maize Ubi1 promoter (ZmUbi), but induced gene expression substantially uniformly in substantially all the tissues.

Example 4

Analysis of Promoter Activity in Each Rice Tissue by Real Time qRT-PCR

Figure 5:
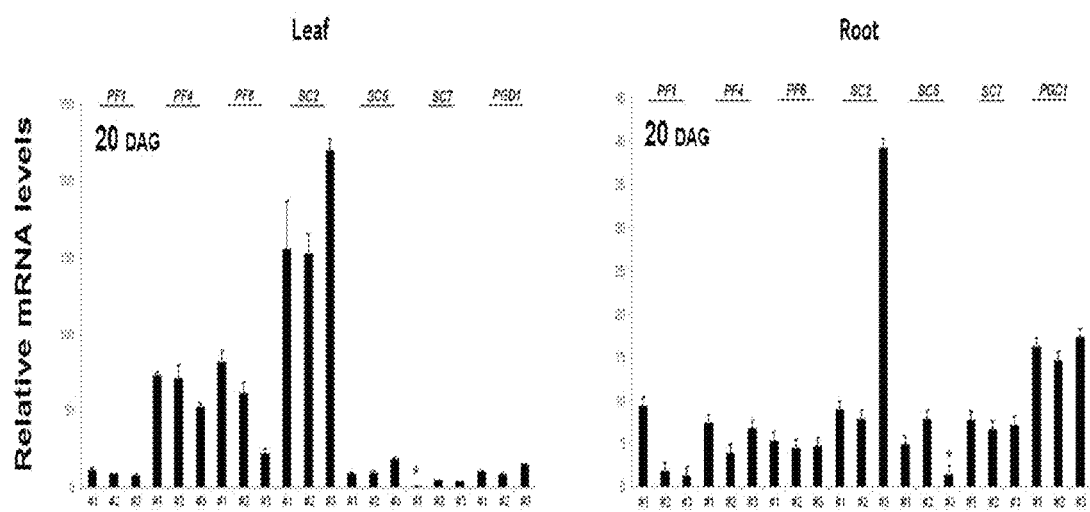
FIG. 5 shows results obtained by quantitatively comparing the expressions of GFP in the leaf and root tissues of 20-day-old the plants according to embodiments.

FIG. 5 shows the results obtained by quantitatively analyzing the expression pattern of the GFP gene according to the activity of each promoter in each tissue of the transformed rice. Similar to in FIG. 4, RNA was extracted from the seeds of the transformed rice and the leaf and root tissues of 20-day-old seedlings. cDNA was synthesized using RNA as a template and amplified by PCR. Then, the PCR product was subjected to real time qRT-PCR analysis using gene-specific primers of GFP used as a target gene. In view of the difference in gene expression according to the variation between events, the analysis of the transformants for each promoter was carried out using 3 events having different promoter insertion sites.

FIG. 5 shows the results obtained by quantitatively analyzing the expression pattern of the GFP gene according to the activity of each promoter in each tissue of the transformed rice. This shows that the activities of the promoters according to the present invention were distributed uniformly in the transformed rice plants in the same manner as in the case of the rice plants transformed with each of the positive control, PGD1.

Example 5

Comparison of Exogenous Promoter Activities Over Three Homozygous Generations

Figure 6:
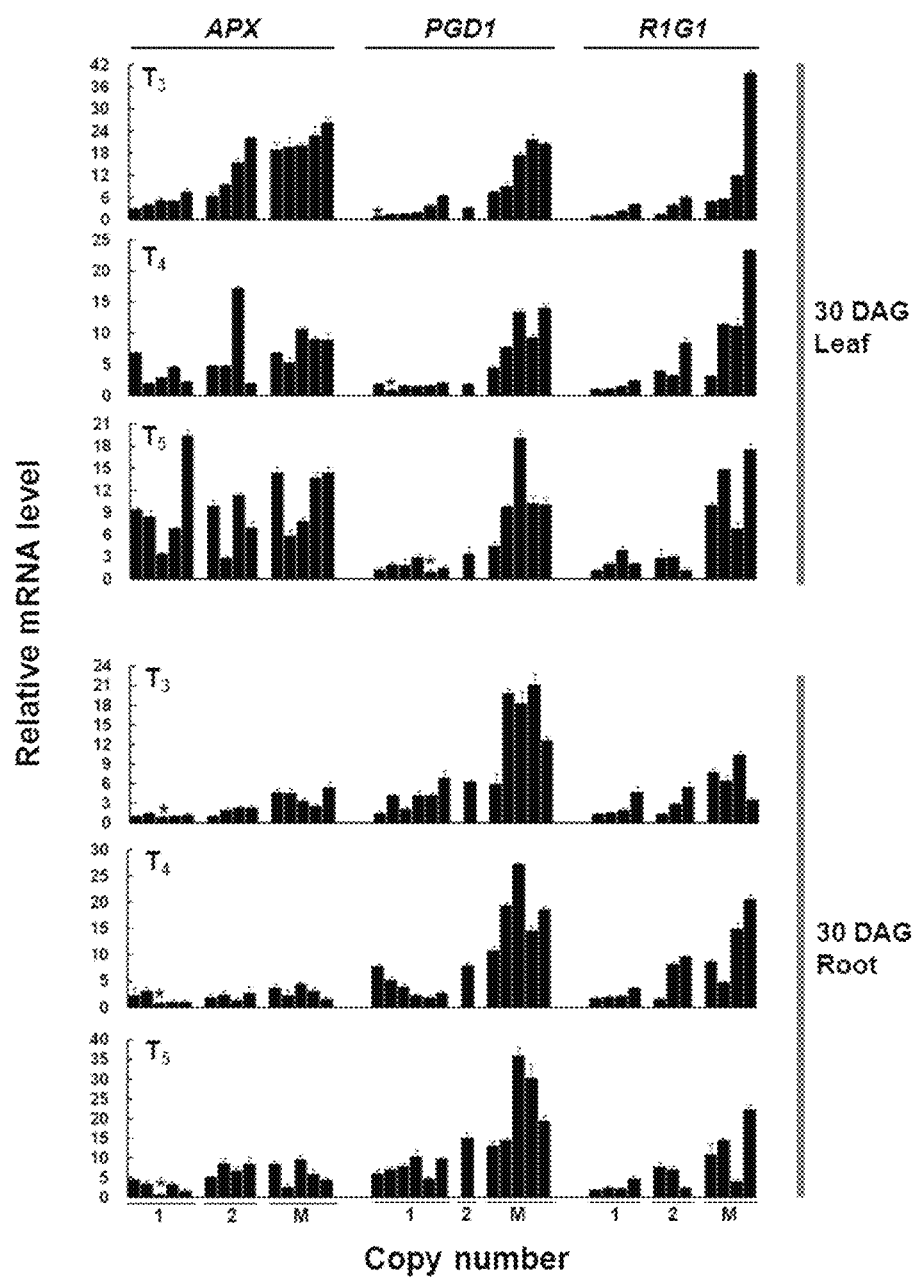
FIG. 6 shows changes in the analyzed promoter activities during three successive generations ($T_3$-$T_5$) according to embodiments.

To investigate whether significant changes occur in the exogenous APX, R1G1 and PGD1 promoter activities over sequential generations in transgenic rice, we measured the respective gfp mRNA levels of $T_3$, $T_4$ and $T_5$ homozygous lines by real-time qPCR using 30 DAG leaf and root tissues. The relative activities among different lines remained similar within each generation (FIG. 6) and the patterns observed in the $T_3$ generation, i.e. that the activity levels of the APX and R1G1 promoters continued to be higher in the leaves and roots, were also observed in the $T_4$ and $T_5$ generations.

Example 6

Figure 7:
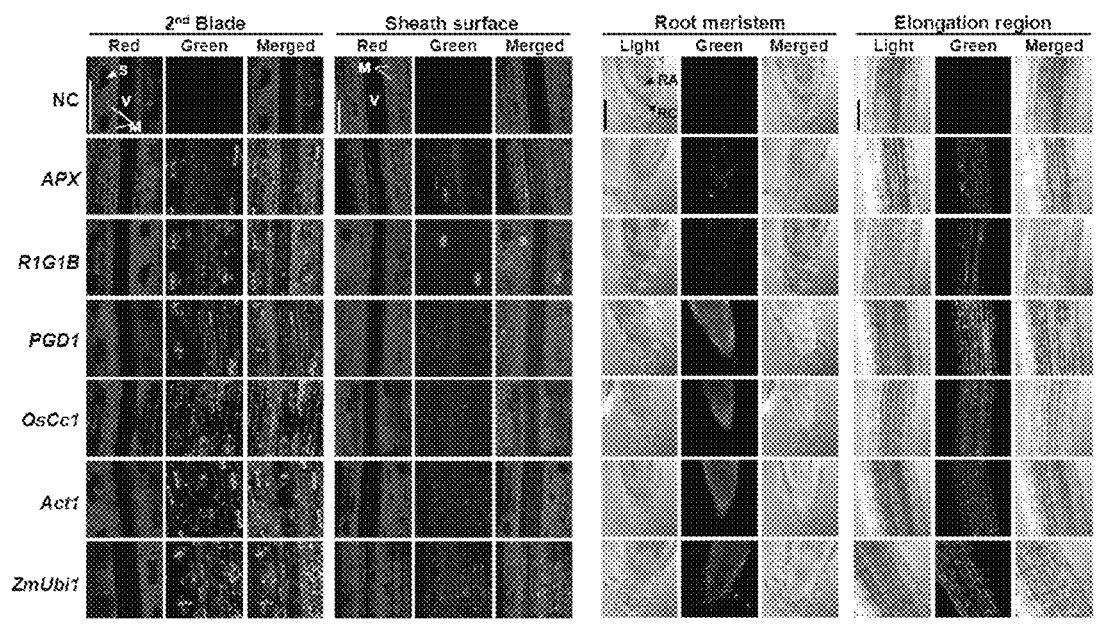
FIGS. 7 and 8 show the expression of GFP fluorescence in the leaf and root of transformed plant according to embodiments.
Figure 8:
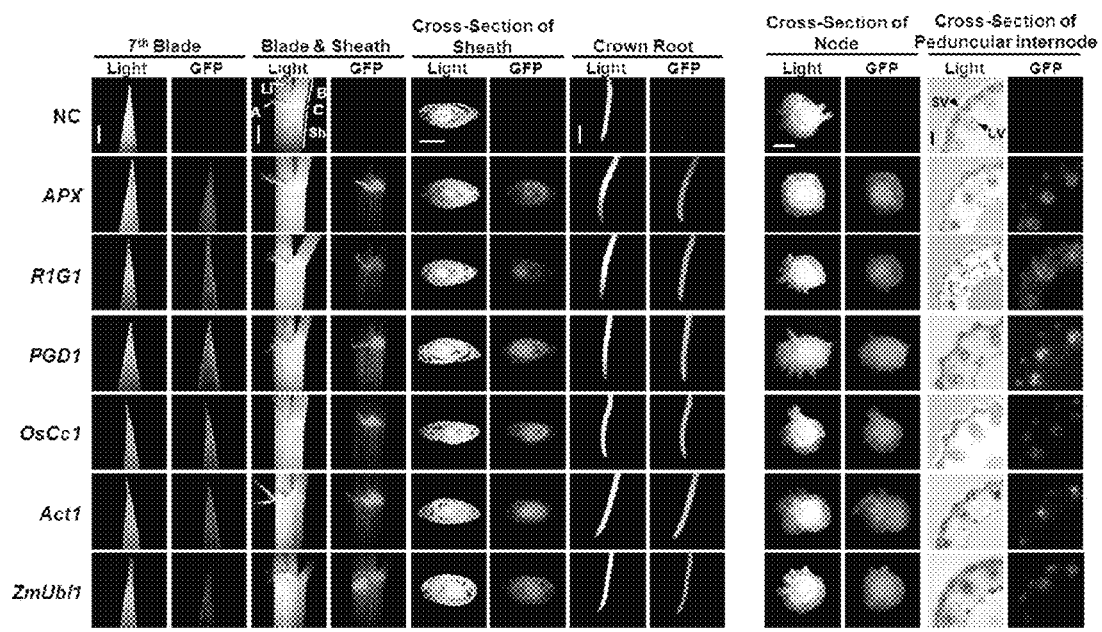
Figure 9:
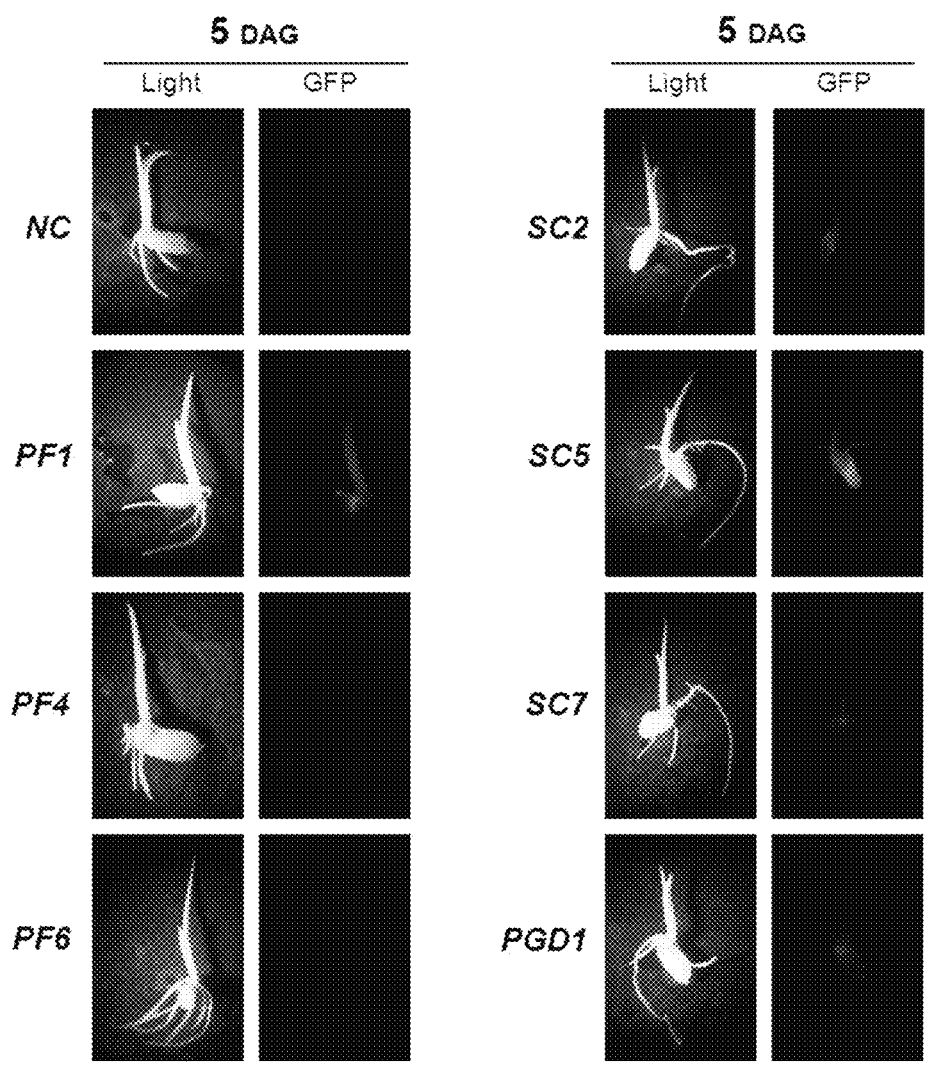
FIG. 9 shows the expression of GFP fluorescence in seedlings of transformed plant according to embodiments.

Observation of GFP Fluorescence in Leaf and Root Tissues of Rice Transformed with Promoter Gene promoter activities in different tissues and/or stages in transgenic rice plants were examined using confocal laser scanning and a fluorescence microscope (FIG. 7). In 7 DAG (days after germination) plants, the levels of GFP fluorescence were high in the vascular bundle sheath and stomatal guard cells, but relatively low in mesophyll cells of the APX:gfp, PGD1:gfp and R1G1:gfp leaves. Levels of GFP fluorescence in root apex, root cap and elongating regions of PGD1:gfp roots were comparable with those of OsCc1, Act1 and ZmUbi1:gfp roots. In contrast, the levels of GFP fluorescence in the corresponding tissues of APX:gfp and R1G1:gfp roots were markedly lower than the others (FIG. 7). We also examined several further tissues at the vegetative stage in promoter:gfp plants. These included the tip of the seventh leaf blade, an area between a leaf blade and a leaf sheath containing the ligule, auricle and collar, a central part of a sheath, and a crown root below a root node (FIG. 8). All three promoters produced GFP fluorescence at high levels in these additional tissues at a similar level to the control promoters (FIG. 8). Stems can be divided into two parts, unelongated and elongated. A region from the node to the nearest crown root of 30 DAG plants representing the unelongated stem showed high levels of GFP fluorescence in all of the promoter: gfp plants examined. A peduncular internode, the longest uppermost internode, is representative of the elongated stem located just below the panicle inflorescence. Large and small vascular bundle (LV and SV, respectively) sheath cells of the peduncular internode also showed high levels of GFP fluorescence in all of the promoter:gfp plants (FIG. 8). To analyze the activities of the promoters used in the present invention, the 5-day-old seedlings of rice plants transformed with each of the promoters (PF1, PF4, PF6, SC2, SC5, and SC7) and GFP fluorescence in the tissues was observed (FIG. 9).

The description of each gene shown in FIG. 7-8 is as follows: V: vascular bundle sheath; S: stomatal guard cells; M: mesophyll cells; RA: root apex; RC: root cap A: auricle; B: base of the leaf blade; C: collar; LI: ligule; Sh: leaf sheath; LV: large vascular bundle; SV: small vascular bundle; NC: negative control Oryza sativa L. cv Nakdong (non-transformed rice): ZmUbi: maize Ubi1 promoter; Act1: rice Actin1 promoter; and OsCc1: rice cytochrome c promoter.

In the leaf and root tissue of the negative control, the expression of GFP fluorescence was not observed, whereas in the leaf and root tissues of the rice plants transformed with the promoters, the expression of GFP fluorescence was clearly and uniformly observed.

This visually shows that the activities of the constitutive expression promoters of the present invention were distributed uniformly in the leaf and root tissues of the transformed rice plants in the same manner as in the case of the rice plants transformed with each of the positive controls, PGD1, ZmUbi, Actin1 and OsCc1.

Example 7

Figure 10:
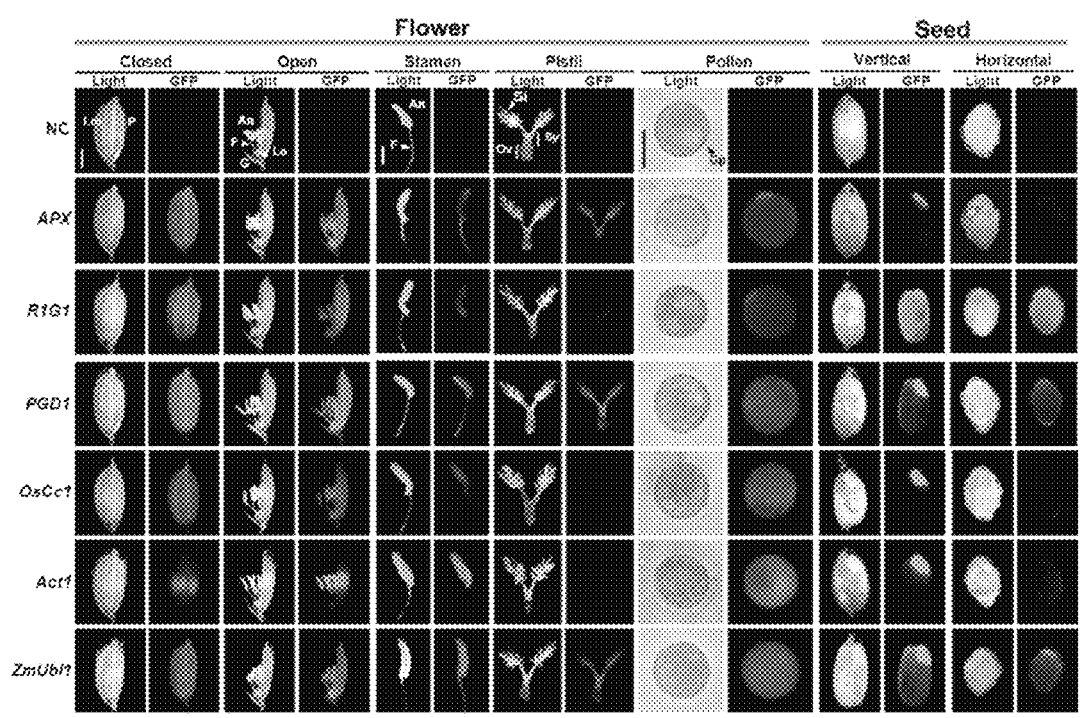
FIG. 10 shows the expression of GFP fluorescence in the flower and seed of transformed plant according to embodiments.

Observation of GFP Fluorescence in Reproductive Organ of Rice Transformed with Promoter GFP fluorescence was further examined in the flowers (spikelets) at the meiosis stage (FIG. 10). As found in the vegetative tissues, the transgenic flowers all showed a high level of GFP fluorescence. More specifically, the PGR1:gfp transgene directed high levels of GFP fluorescence in all of the floral organs including the lemma, palea, lodicule, glume, anther, filament, stigma, style, ovary and pollen, in a manner similar to ZmUbi1:gfp. GFP fluorescence in the APX:gfp flowers was also similar to that found for PGR1:gfp and ZmUbi1:gfp in all floral organs except for the ovary where no signal could be detected. In addition, zero or very low levels of GFP fluorescence were observed in a whole pistil and a filament of the stamen in the OsCc1:gfp, Act1:gfp and R1G1:gfp flowers. Hence, the APX and R1G1 promoters were found to be highly active in the whole plant body at both the vegetative and reproductive. Interestingly, the spatial activities of the PGD1 promoter were found to be strikingly similar to those of the ZmUbi1, a widely used constitutive promoter.

In the case of the APX promoter isolated in the present invention, GFP fluorescence was observed in the seed embryo in a manner similar to the case of OsCc1 and Act1. In the case of PGD1 and R1G1 promoters, GFP fluorescence was observed in all the embryo and endosperm in a manner similar to the case of ZmUbi. In the case of the R1G1 promoter, the uniform expression of GFP fluorescence was observed in the flower of the transformed rice. Particularly, in the case of the APX and PGD1 promoters, outstanding GFP fluorescence was observed in the flower anther and ovary.

As a result, in the case of the above-described constitutive expression promoters, GFP fluorescence was observed uniformly in all the tissues of the rice plants, including seeds and flowers.

The description of each gene shown in FIG. 10 is as follows: An: anther; F: filament; G: glume; Gp: germ pore; Lm: lemma; Lo: lodicule; Ov: ovary; P: palea; Si: stigma;

Sy: style; NC: negative control *Oryza sativa* L. cv *Nakdong* (non-transformed rice): ZmUbi: maize Ubi1 promoter; Act1: rice Actin1 promoter; and OsCc1: rice cytochrome c promoter.

Example 8

Levels of GFP Protein in the Promoter:gfp Transgenic Rice Plants

Figure 11:
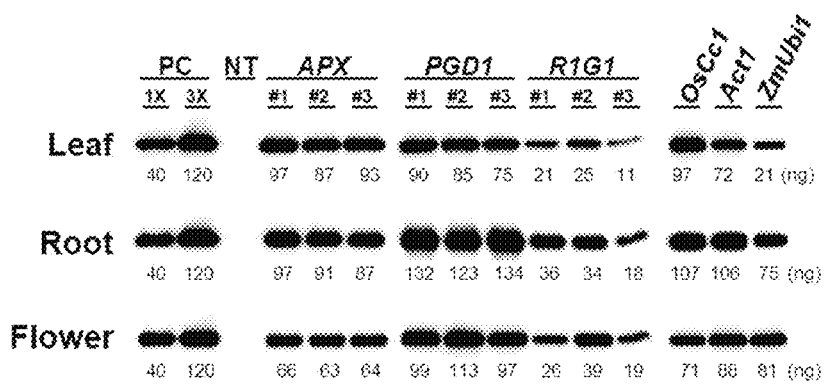
FIG. 11 shows levels of GFP protein in the promoter: gfp transgenic plants according to embodiments.

Protein extracts were prepared from the leaf and root tissues at 30 DAG and from flowers just before pollination. Three independent promoter:gfp transgenic plants and non-transgenic (NT) plants were analyzed. One line of each of the transgenic plants harboring the OsCc1, Act1 and ZmUbi1 gene promoters were included as constitutive controls. Ten μg of total soluble proteins were separated on a SDS-polyacrylamide gel, transferred to a membrane, and then immunoblotted with an anti-GFP antibody. The amount of GFP protein in promoter:gfp transgenic plants were calculated by comparing band intensities with those of known amounts of recombinant GFP protein used as positive controls (PC). The GFP protein levels of APX:gfp and PGR1:gfp plants were high and comparable to those of OsCc1:gfp, Act1:gfp and ZmUbi1:gfp plants (0.6 to 1.3% of the total soluble proteins; FIG. 11.). The GFP protein levels of R1G1:gfp plants ranged from 0.11 to 0.34% of the total soluble proteins depending on the specific transgenic lines and/or tissues.

What is claimed is:

1. A method comprising:
   producing a target protein by transforming a plant using a vector comprising a promoter consisting of SEQ ID NO: 6 operably linked to a gene encoding said target protein.

2. The method of claim 1, wherein the target protein comprises at least one of interleukin, interferon, platelet-derived growth factor, hemoglobin, elastin, collagen, insulin, fibroblast growth factor, human growth factor, human serum albumin and erythropoietin.

3. A method comprising:
   transforming a plant cell with a vector comprising a promoter consisting of SEQ ID NO: 6 operably linked to a gene coding sequence; and
   redifferentiating a transformed plant from the transformed plant cell.

* * * * *